(12) United States Patent
Lindekugel et al.

(10) Patent No.: US 12,207,840 B2
(45) Date of Patent: Jan. 28, 2025

(54) MAGNETIZING SYSTEM FOR NEEDLE ASSEMBLIES

(71) Applicant: Bard Access Systems, Inc., Salt Lake City, UT (US)

(72) Inventors: Eric W. Lindekugel, Salt Lake City, UT (US); Matthew J. Prince, Herriman, UT (US)

(73) Assignee: Bard Access Systems, Inc., Salt Lake City, UT (US)

( * ) Notice: Subject to any disclaimer, the term of this patent is extended or adjusted under 35 U.S.C. 154(b) by 0 days.

(21) Appl. No.: 17/850,468

(22) Filed: Jun. 27, 2022

(65) Prior Publication Data
US 2022/0323101 A1 Oct. 13, 2022

Related U.S. Application Data

(63) Continuation of application No. 15/965,419, filed on Apr. 27, 2018, now Pat. No. 11,369,410.
(Continued)

(51) Int. Cl.
*A61B 17/34* (2006.01)
*A61B 8/00* (2006.01)
(Continued)

(52) U.S. Cl.
CPC ........ *A61B 17/3403* (2013.01); *A61B 8/0841* (2013.01); *A61B 8/085* (2013.01);
(Continued)

(58) Field of Classification Search
CPC ... A61B 17/3403; A61B 8/0841; A61B 8/085; A61B 8/0891; A61B 8/4427;
(Continued)

(56) References Cited

U.S. PATENT DOCUMENTS 3,409,853 A 11/1968 Guerth
3,467,926 A 9/1969 Smith
(Continued)

FOREIGN PATENT DOCUMENTS

CN 105025787 A 11/2015
CN 105232047 A 1/2016
(Continued)

OTHER PUBLICATIONS

EP 18790656.5 filed Nov. 27, 2019 Supplementary European Search Report dated Apr. 9, 2020.
(Continued)

*Primary Examiner* — Mohamad A Musleh
(74) *Attorney, Agent, or Firm* — Rutan & Tucker LLP

(57) ABSTRACT

A magnetizing system for use in selectively magnetizing a needle of a medical device is disclosed. Once magnetized, the needle can be tracked by a needle guidance system, which assists the clinician placing the needle by visualizing on a display the position and orientation of the needle after its insertion into a body of a patient. An orientation key system is included with the magnetizing system to ensure the needle is positioned correctly in the magnetizing system. This in turn ensures that the needle is properly magnetized so as to be accurately tracked by the needle guidance system. In one embodiment a first key is included with the magnetizing system and configured to cooperatively mate with a second key included with the needle of the medical device. Various types of keys are disclosed herein.

11 Claims, 20 Drawing Sheets

Related U.S. Application Data

(60) Provisional application No. 62/491,037, filed on Apr. 27, 2017.

(51) Int. Cl.
| | |
|---|---|
| *A61B 8/08* | (2006.01) |
| *A61B 34/00* | (2016.01) |
| *A61B 34/20* | (2016.01) |
| *A61B 90/11* | (2016.01) |
| *A61B 90/96* | (2016.01) |
| *A61B 90/98* | (2016.01) |
| *H01F 7/02* | (2006.01) |
| *A61B 5/06* | (2006.01) |
| *A61B 17/00* | (2006.01) |
| *A61B 90/00* | (2016.01) |

(52) U.S. Cl.
CPC .......... *A61B 8/0891* (2013.01); *A61B 8/4427* (2013.01); *A61B 34/20* (2016.02); *A61B 34/73* (2016.02); *A61B 90/11* (2016.02); *A61B 90/96* (2016.02); *A61B 90/98* (2016.02); *H01F 7/021* (2013.01); *A61B 5/062* (2013.01); *A61B 5/066* (2013.01); *A61B 8/4254* (2013.01); *A61B 8/463* (2013.01); *A61B 2017/00199* (2013.01); *A61B 2017/3413* (2013.01); *A61B 2034/2051* (2016.02); *A61B 2034/2063* (2016.02); *A61B 90/37* (2016.02); *A61B 2090/378* (2016.02); *A61B 2090/3784* (2016.02)

(58) Field of Classification Search
CPC .......... A61B 34/20; A61B 34/73; A61B 90/11; A61B 90/96; A61B 90/98; A61B 5/062; A61B 5/066; A61B 8/4254; A61B 8/463; A61B 90/37; A61B 2017/00199; A61B 2017/3413; A61B 2034/2051; A61B 2034/2063; A61B 2090/378; A61B 2090/3784; A61B 8/526; H01F 7/021
See application file for complete search history.

(56) References Cited

U.S. PATENT DOCUMENTS

| | | | |
|---|---|---|---|
| 3,847,157 A | 11/1974 | Caillouette et al. | |
| 4,063,561 A | 12/1977 | McKenna | |
| 4,161,943 A | 7/1979 | Nogier | |
| 4,237,518 A | 12/1980 | Krulwich | |
| 4,458,705 A | 7/1984 | Cawood | |
| 4,529,954 A | 7/1985 | Steingroever et al. | |
| 4,633,237 A | 12/1986 | Tucknott et al. | |
| 5,055,813 A | 10/1991 | Johnson | |
| 5,659,279 A | 8/1997 | Janssen et al. | |
| 5,803,089 A | 9/1998 | Ferre et al. | |
| 5,845,646 A | 12/1998 | Lemelson | |
| 6,154,352 A | 11/2000 | Atallah | |
| 6,249,199 B1 | 6/2001 | Liu | |
| 6,310,532 B1 | 10/2001 | Santa Cruz et al. | |
| 6,432,036 B1 | 8/2002 | Kim | |
| 7,023,309 B2 | 4/2006 | Laskaris et al. | |
| 7,090,639 B2 | 8/2006 | Govari | |
| 7,135,978 B2 | 11/2006 | Gisselberg et al. | |
| 7,214,191 B2 | 5/2007 | Stringer et al. | |
| 7,775,215 B2 | 8/2010 | Hassler, Jr. et al. | |
| 7,775,966 B2 | 8/2010 | Dlugos et al. | |
| 7,850,006 B2 | 12/2010 | Uchiyama | |
| 7,873,401 B2 | 1/2011 | Shachar | |
| 7,887,516 B2 | 2/2011 | Young | |
| 7,927,270 B2 | 4/2011 | Dlugos et al. | |
| 8,016,744 B2 | 9/2011 | Dlugos et al. | |
| 8,016,745 B2 | 9/2011 | Hassler, Jr. et al. | |
| 8,174,346 B1 | 5/2012 | Koren | |
| 8,240,211 B2 | 8/2012 | Zeitner et al. | |
| 8,388,541 B2 | 3/2013 | Messerly et al. | |
| 8,475,407 B2 | 7/2013 | Kalpin et al. | |
| 8,483,802 B2 | 7/2013 | Kalpin et al. | |
| 8,532,743 B2 | 9/2013 | Stangenes et al. | |
| 8,622,975 B2 | 1/2014 | Andreoni et al. | |
| 8,725,435 B2 | 5/2014 | Snow et al. | |
| 8,781,555 B2 | 7/2014 | Burnside et al. | |
| 8,840,541 B2 | 9/2014 | Snow et al. | |
| 8,849,382 B2 | 9/2014 | Cox et al. | |
| 8,939,888 B2 | 1/2015 | Augarten et al. | |
| 9,017,283 B2 | 4/2015 | Birchard et al. | |
| 9,113,812 B2 | 8/2015 | Kalpin et al. | |
| 9,155,517 B2 | 10/2015 | Dunbar et al. | |
| 9,216,257 B2 | 12/2015 | Kalpin et al. | |
| 9,224,529 B2 | 12/2015 | Gery | |
| 9,257,220 B2 | 2/2016 | Nicholls et al. | |
| 9,299,925 B2 | 3/2016 | Yi et al. | |
| 9,308,022 B2 | 4/2016 | Chitre et al. | |
| 9,339,601 B2 | 5/2016 | Kalpin et al. | |
| 9,439,653 B2 | 9/2016 | Avneri et al. | |
| 9,456,766 B2 | 10/2016 | Cox et al. | |
| 9,459,087 B2 | 10/2016 | Dunbar et al. | |
| 9,492,097 B2 | 11/2016 | Wilkes et al. | |
| 9,517,299 B2 | 12/2016 | Tieck et al. | |
| 9,521,961 B2 | 12/2016 | Silverstein et al. | |
| 9,554,716 B2 | 1/2017 | Burnside et al. | |
| 9,597,008 B2 | 3/2017 | Henkel et al. | |
| 9,636,031 B2 | 5/2017 | Cox | |
| 9,649,048 B2 | 5/2017 | Cox et al. | |
| 9,744,291 B2 | 8/2017 | Tieck et al. | |
| 10,032,552 B2 | 7/2018 | Ma et al. | |
| 10,449,330 B2 | 10/2019 | Newman et al. | |
| 10,524,691 B2 | 1/2020 | Newman et al. | |
| 10,751,509 B2 | 8/2020 | Misener | |
| 11,344,220 B2 | 5/2022 | Burkholz et al. | |
| 11,369,410 B2 | 6/2022 | Lindekugel | |
| 2003/0040671 A1 | 2/2003 | Somogyi et al. | |
| 2003/0052785 A1 | 3/2003 | Gisselberg et al. | |
| 2004/0019447 A1 | 1/2004 | Shachar | |
| 2004/0051610 A1 | 3/2004 | Sajan | |
| 2005/0059884 A1 | 3/2005 | Krag | |
| 2006/0114088 A1 | 6/2006 | Shachar | |
| 2006/0211914 A1 | 9/2006 | Hassler et al. | |
| 2007/0244373 A1 | 10/2007 | Osypka | |
| 2007/0290654 A1 | 12/2007 | Govari et al. | |
| 2008/0049367 A1 | 2/2008 | Carson et al. | |
| 2008/0146939 A1 | 6/2008 | McMorrow et al. | |
| 2010/0043561 A1 | 2/2010 | Zeitner et al. | |
| 2010/0096553 A1 | 4/2010 | Patil et al. | |
| 2010/0210950 A1 | 8/2010 | Dunbar et al. | |
| 2011/0060185 A1 | 3/2011 | Ikuma et al. | |
| 2011/0196235 A1 | 8/2011 | Dunbar et al. | |
| 2011/0237936 A1 | 9/2011 | Kalpin et al. | |
| 2011/0237937 A1 | 9/2011 | Kalpin et al. | |
| 2013/0150714 A1 | 6/2013 | Howlett et al. | |
| 2013/0296691 A1 | 11/2013 | Ashe | |
| 2014/0031674 A1 | 1/2014 | Newman et al. | |
| 2014/0165796 A1 | 6/2014 | Gauthier et al. | |
| 2014/0253270 A1* | 9/2014 | Nicholls ................ A61B 5/062 |
| | | | 335/284 |
| 2014/0257080 A1 | 9/2014 | Dunbar et al. | |
| 2014/0257104 A1 | 9/2014 | Dunbar et al. | |
| 2014/0257746 A1 | 9/2014 | Dunbar et al. | |
| 2015/0080710 A1 | 3/2015 | Henkel et al. | |
| 2015/0359991 A1 | 12/2015 | Dunbar et al. | |
| 2015/0365787 A1 | 12/2015 | Farrell | |
| 2016/0015472 A1 | 1/2016 | Tiernan et al. | |
| 2016/0351312 A1 | 12/2016 | Koren | |
| 2017/0007200 A1 | 1/2017 | Hagy et al. | |
| 2017/0079548 A1* | 3/2017 | Silverstein ........... A61B 8/0841 |
| 2017/0079549 A1 | 3/2017 | Henkel et al. | |
| 2017/0079550 A1 | 3/2017 | Henkel et al. | |
| 2017/0079551 A1 | 3/2017 | Henkel et al. | |
| 2017/0126864 A1 | 5/2017 | Lim et al. | |
| 2017/0261564 A1 | 9/2017 | Gabrys et al. | |
| 2017/0325713 A1 | 11/2017 | Burkholz et al. | |
| 2017/0326342 A1 | 11/2017 | Ma et al. | |
| 2018/0061546 A1 | 3/2018 | Ma et al. | |

(56) References Cited

U.S. PATENT DOCUMENTS

| | | |
|---|---|---|
| 2018/0289929 A1 | 10/2018 | Ma et al. |
| 2018/0310955 A1 | 11/2018 | Lindekugel et al. |
| 2019/0298221 A1 | 10/2019 | Sonderegger |
| 2020/0360662 A1 | 11/2020 | Ma et al. |
| 2021/0065857 A1 | 3/2021 | Newman et al. |
| 2021/0169585 A1 | 6/2021 | Prince et al. |
| 2022/0105324 A1 | 4/2022 | Broniec et al. |
| 2022/0142501 A1 | 5/2022 | Prince et al. |
| 2022/0142502 A1 | 5/2022 | Prince et al. |
| 2022/0401158 A1 | 12/2022 | Sowards et al. |
| 2023/0006443 A1 | 1/2023 | Patankar et al. |
| 2024/0090793 A1 | 3/2024 | Prince et al. |

FOREIGN PATENT DOCUMENTS

| | | |
|---|---|---|
| CN | 103945772 B | 9/2016 |
| CN | 105073067 B | 6/2017 |
| DE | 102006033229 B4 | 5/2013 |
| EP | 2015105 B1 | 6/2011 |
| EP | 2730306 A1 | 5/2014 |
| EP | 2285287 B1 | 4/2015 |
| EP | 2939599 A2 | 11/2015 |
| EP | 2939601 A2 | 11/2015 |
| EP | 2997901 A1 | 3/2016 |
| EP | 2753243 B1 | 4/2016 |
| JP | 5349582 B2 | 11/2013 |
| JP | 5908981 B2 | 4/2016 |
| JP | 6242421 B2 | 12/2017 |
| KR | 20150123233 A | 11/2015 |
| WO | 2008009442 A2 | 1/2008 |
| WO | 2009010386 A1 | 1/2009 |
| WO | 2009129845 A1 | 10/2009 |
| WO | 2013034175 A1 | 3/2013 |
| WO | 2013142386 A1 | 9/2013 |
| WO | 2014/062728 A1 | 4/2014 |
| WO | 2014135592 A1 | 9/2014 |
| WO | 16096190 A1 | 6/2016 |
| WO | 17016961 A1 | 2/2017 |
| WO | 2018/201053 A1 | 11/2018 |
| WO | 2022/099147 A1 | 5/2022 |
| WO | 2022103772 A1 | 5/2022 |
| WO | 2022271864 A1 | 12/2022 |
| WO | 2023009446 A1 | 2/2023 |

OTHER PUBLICATIONS

EP 221711096 filed May 2, 2022, Extended European Search Report dated Jul. 22, 2022.
EP20202521.9 filed Oct. 19, 2020 Extended European Search Report dated Jan. 28, 2021.
PCT/US2018/029958 filed Apr. 27, 2018 Communication Pursuant to Rules 70(2) and 70a(2) dated Apr. 29, 2020.
PCT/US2018/029958 filed Apr. 27, 2018 International Search Report and Written Opinion dated Jul. 11, 2018.
PCT/US2018/029958 filed Apr. 27, 2018 International Search Report dated Apr. 27, 2018.
U.S. Appl. No. 15/965,419, filed Apr. 27, 2018 Final Office Action dated Jan. 15, 2021.
U.S. Appl. No. 15/965,419, filed Apr. 27, 2018 Non-Final Office Action dated Aug. 6, 2021.
U.S. Appl. No. 15/965,419, filed Apr. 27, 2018 Non-Final Office Action dated Sep. 24, 2020.
U.S. Appl. No. 15/965,419, filed Apr. 27, 2018 Notice of Allowance dated Feb. 16, 2022.
PCT/US2022/034584 filed Jun. 22, 2022, International Preliminary Report on Patentability dated Dec. 14, 2023.
U.S. Appl. No. 17/521,680, filed Nov. 8, 2021 Notice of Allowance dated Oct. 11, 2023.
U.S. Appl. No. 17/522,828, filed Nov. 9, 2021 Non-Final Office Action dated Nov. 9, 2023.
U.S. Appl. No. 17/522,828, filed Nov. 9, 2021 Notice of Allowance dated Apr. 3, 2024.
U.S. Appl. No. 17/846,973, filed Jun. 22, 2022 Non-Final Office Action dated Jun. 12, 2024.
U.S. Appl. No. 17/872,814, filed Jul. 25, 2022 Non-Final Office Action dated Jul. 10, 2024.
PCT/US2021/058667 filed Nov. 9, 2021 International Search Report and Written Opinion dated Mar. 1, 2022.
PCT/US2022/038202 filed Jul. 25, 2022 International Search Report and Written Opinion dated Nov. 14, 2022.
U.S. Appl. No. 17/521,680, filed Nov. 8, 2021 Non-Final Office Action dated Jun. 2, 2023.
PCT/US2021/058478 filed Nov. 8, 2021 International Search Report and Written Opinion dated Mar. 1, 2022.
PCT/US2022/034584 filed Jun. 22, 2022, International Search Report and Written Opinion dated Oct. 10, 2022.

* cited by examiner

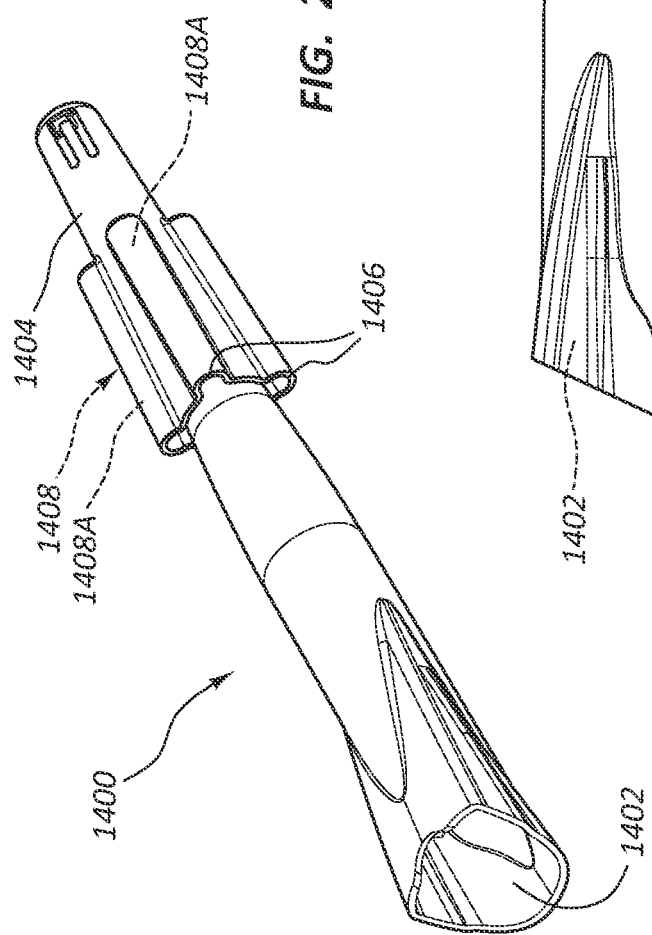
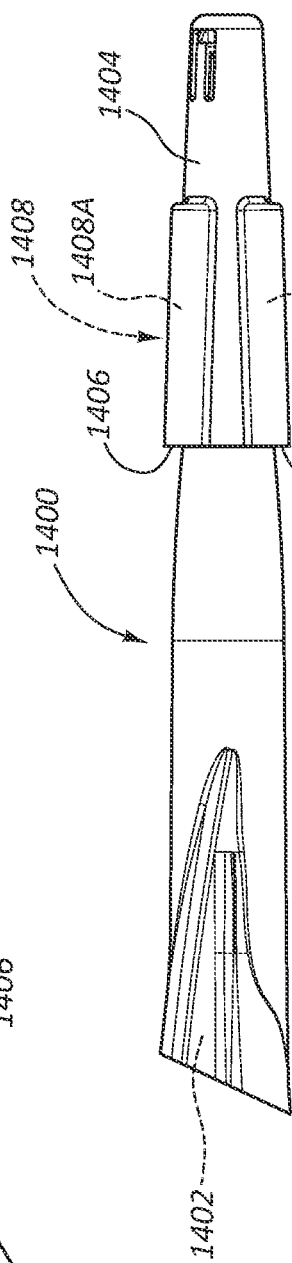
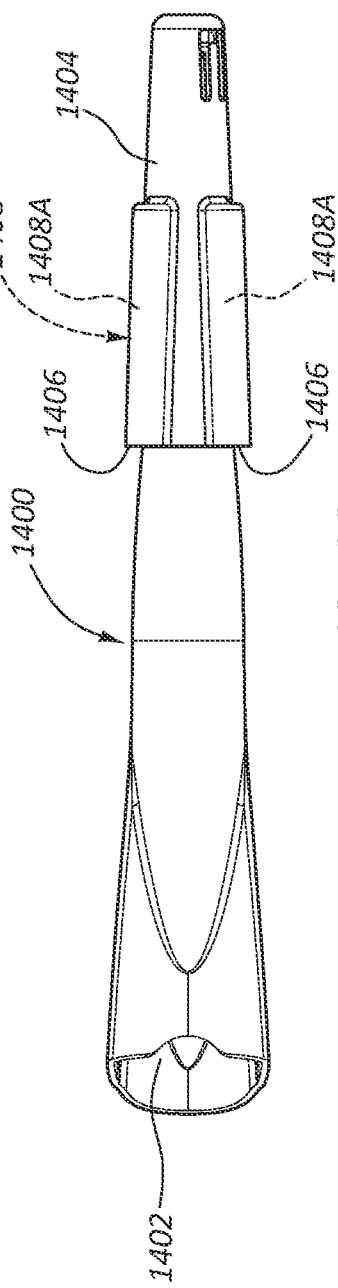
FIG. 2A
FIG. 2B
FIG. 2C

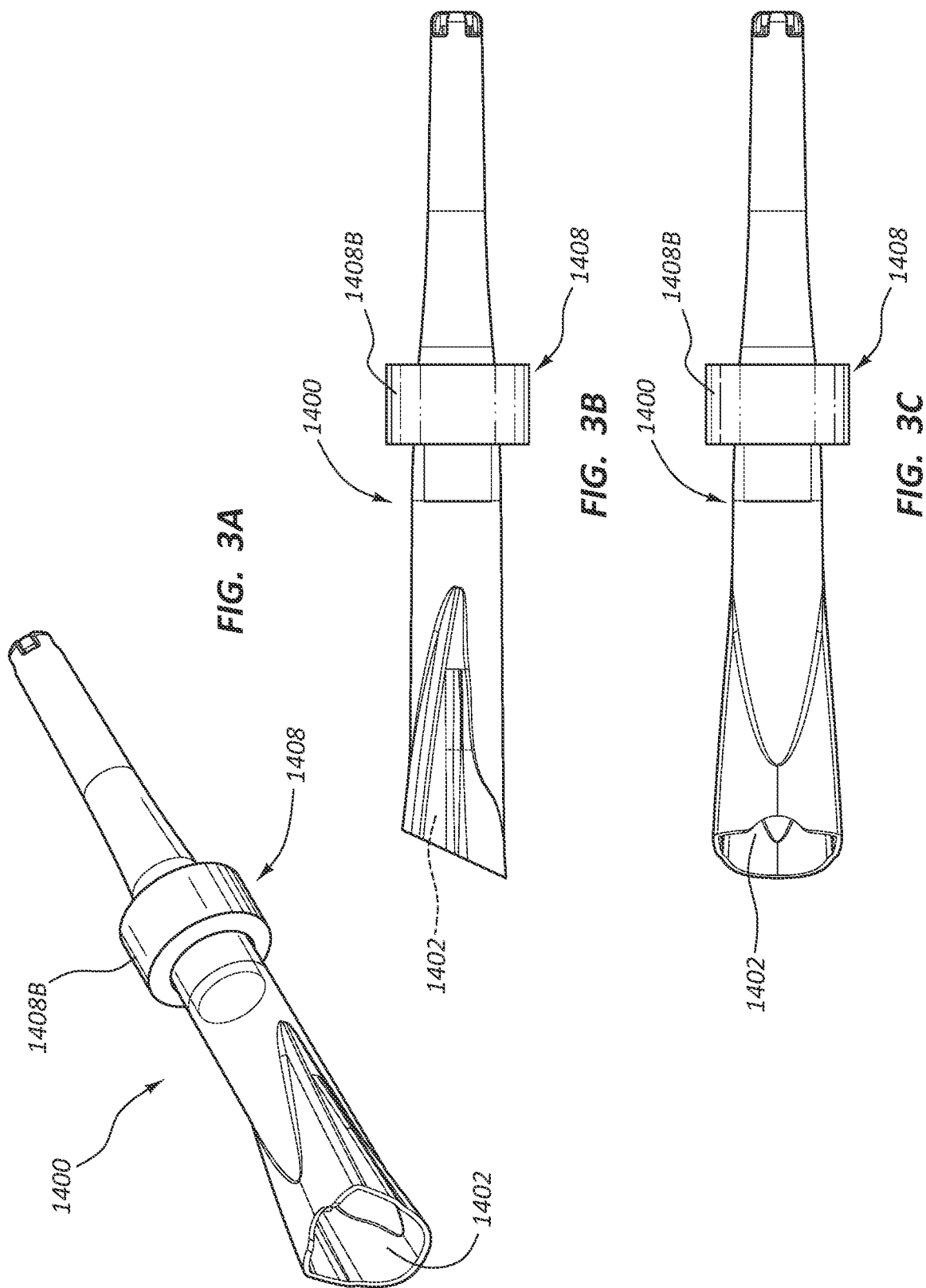

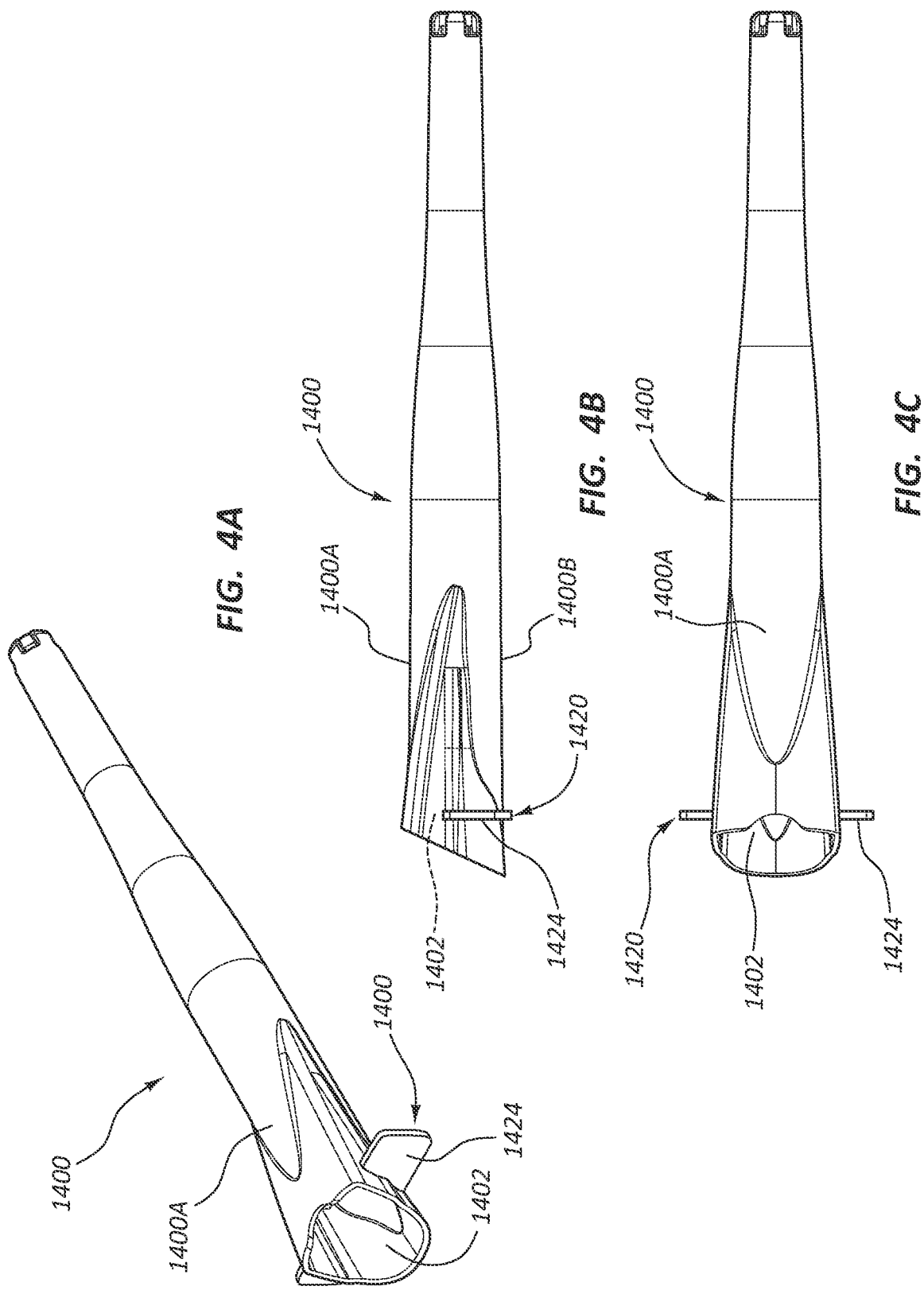

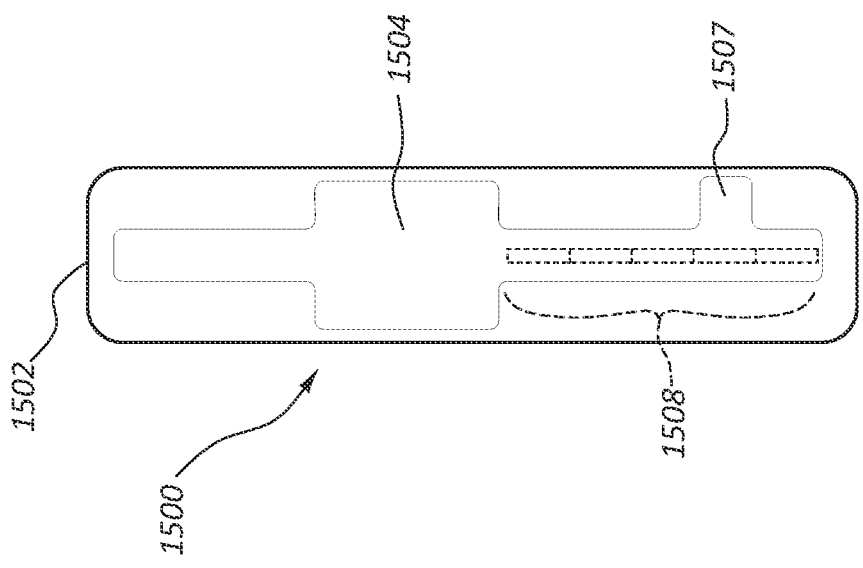
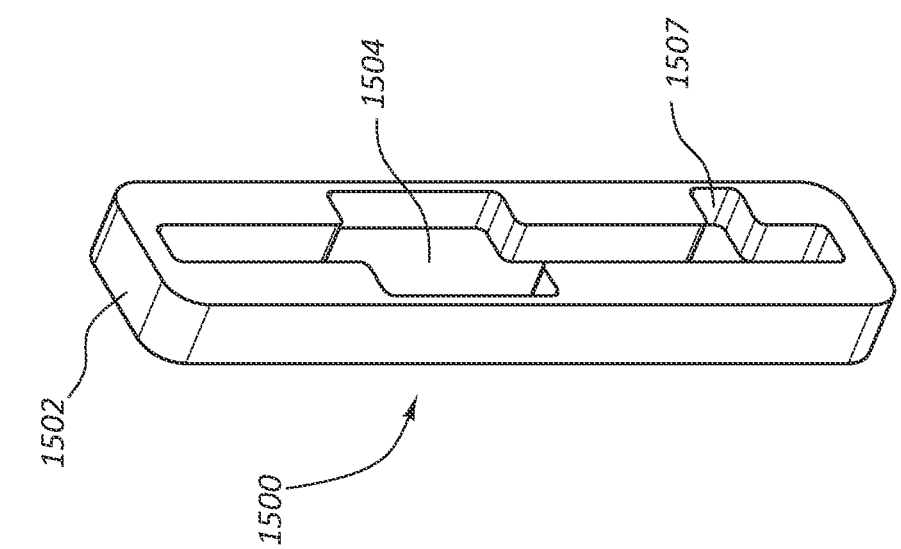

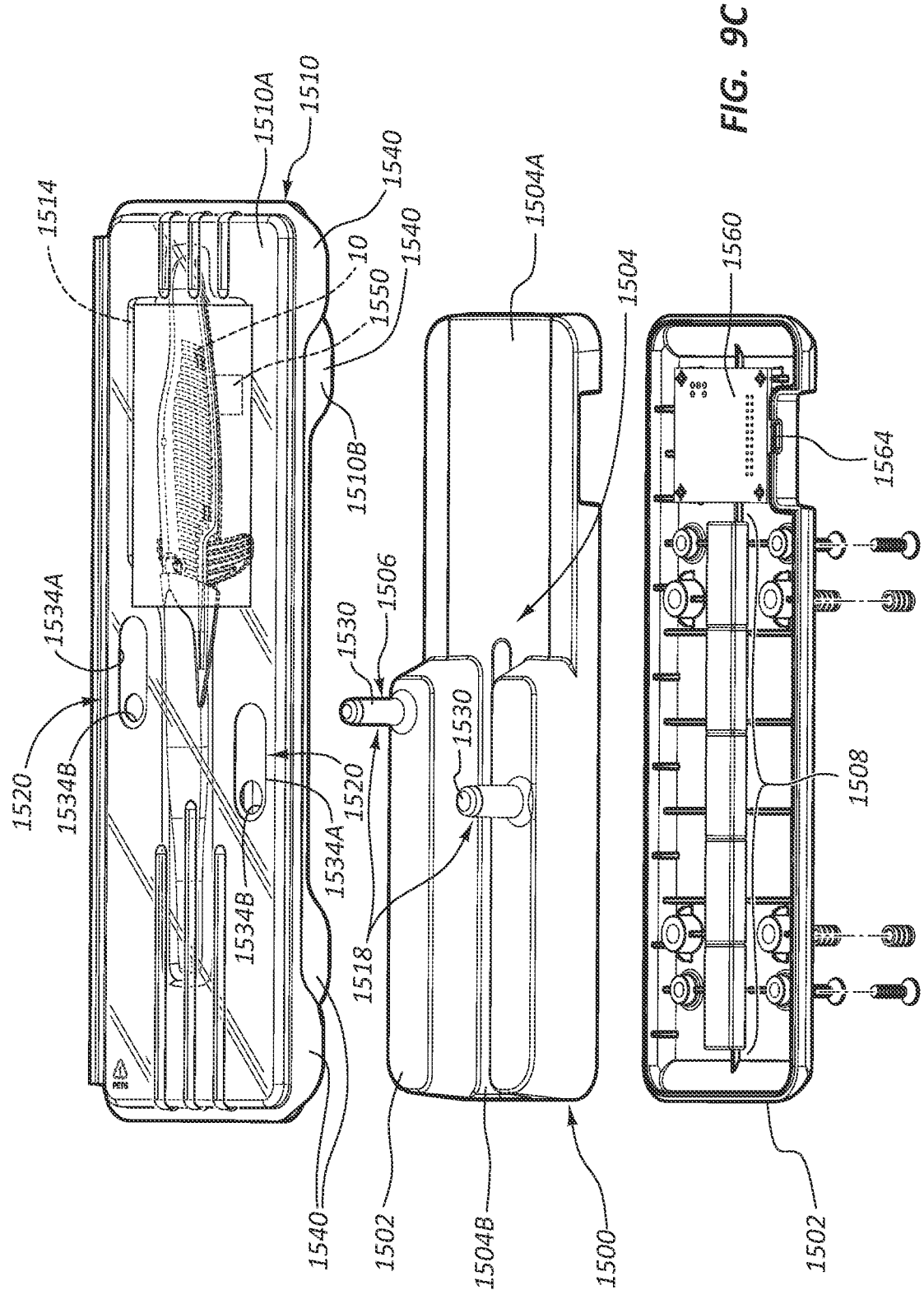

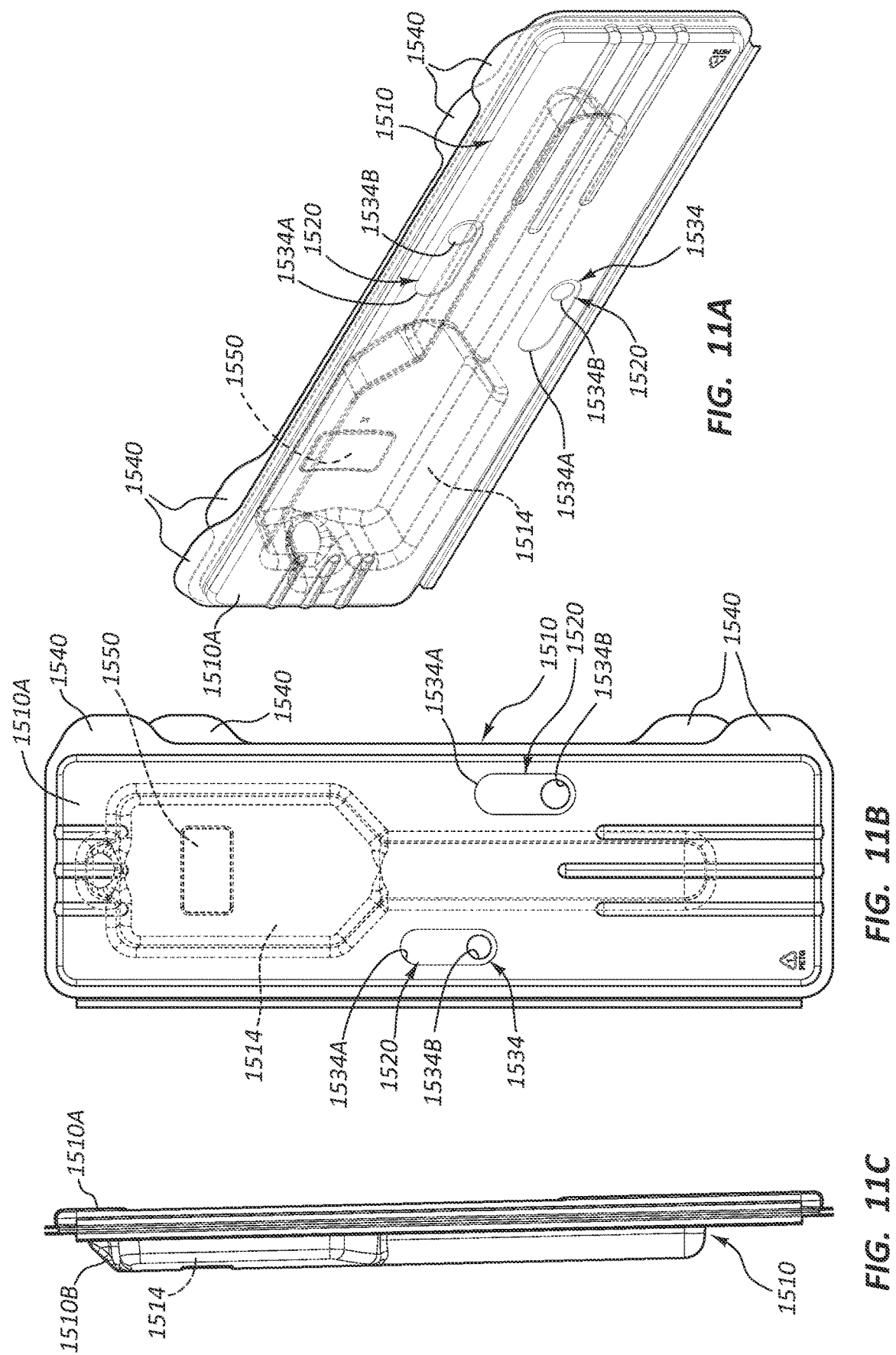

MAGNETIZING SYSTEM FOR NEEDLE ASSEMBLIES

CROSS-REFERENCE TO RELATED APPLICATIONS

This application is a continuation of U.S. patent application Ser. No. 15/965,419, filed Apr. 27, 2018, now U.S. Pat. No. 11,369,410, which claims the benefit of priority to U.S. Provisional Application No. 62/491,037, filed Apr. 27, 2017, and titled "Magnetizing System for Needle Assemblies," each of which is incorporated by reference in its entirety into this application.

BRIEF SUMMARY

Briefly summarized, embodiments of the present invention are directed to a magnetizing system for use in selectively magnetizing a needle (or other cannula or magnetizable component for insertion into a patient) of a medical device. Once magnetized, the needle can be tracked by a needle guidance system, which assists the clinician placing the needle by visualizing the position and orientation of the needle after its insertion into a body of a patient. The image of the needle produced by the needle guidance system is superimposed in one embodiment atop an ultrasound image of an internal body portion, such as an imaged vein or other vessel, to enable the clinician to accurately place the needle in a desired location, such as within the lumen of the vein, for instance.

Embodiments herein are also directed to an orientation key system included with the magnetizing system to ensure the needle is positioned correctly in the magnetizing system. This in turn ensures that the needle is properly magnetized so as to be accurately tracked by the needle guidance system. In one embodiment a first key is included with the magnetizing system and configured to cooperatively mate with a second key included with the needle of the medical device. Various types of keys are disclosed herein.

These and other features of embodiments of the present invention will become more fully apparent from the following description and appended claims, or may be learned by the practice of embodiments of the invention as set forth hereinafter.

BRIEF DESCRIPTION OF THE DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which:

FIGS. 2A-2D depict various views of a needle cover for use with the catheter insertion device of FIGS. 1A and 1B according to one embodiment;

FIGS. 3A-3C depict various views of a needle cover according to one embodiment;

FIGS. 4A-4C depict various views of a needle cover according to one embodiment;

FIGS. 6A-6C depict various views of the magnetizer of FIG. 5;

FIGS. 9A-9C are various views of a magnetizer and tray assembly according to one embodiment;

FIGS. 11A-11C depict various views of the tray of FIGS. 9A-9C;

DETAILED DESCRIPTION OF SELECTED EMBODIMENTS

Reference will now be made to figures wherein like structures will be provided with like reference designations. It is understood that the drawings are diagrammatic and schematic representations of exemplary embodiments of the present invention, and are neither limiting nor necessarily drawn to scale.

For clarity it is to be understood that the word "proximal" refers to a direction relatively closer to a clinician using the device to be described herein, while the word "distal" refers to a direction relatively further from the clinician. For example, the end of a catheter placed within the body of a patient is considered a distal end of the catheter, while the catheter end remaining outside the body is a proximal end of the catheter. Also, the words "including," "has," and "having," as used herein, including the claims, shall have the same meaning as the word "comprising."

Embodiments herein are generally directed to a magnetizing system for use in selectively magnetizing a needle (or other magnetizable cannula, tissue-penetrating component, or medical component for insertion into a patient) of a medical device. Once magnetized, the needle can be tracked by a needle guidance system, which assists the clinician placing the needle by visualizing the position and orientation of the needle after its insertion into a body of a patient. The image of the needle produced by the needle guidance system is superimposed in one embodiment atop an ultrasound image of an internal body portion, such as an imaged vein or other vessel, to enable the clinician to accurately place the needle in a desired location, such as within the lumen of the vein, for instance.

Embodiments herein are also directed to an orientation key system included with the magnetizing system to ensure the needle is positioned correctly in the magnetizing system. This in turn ensures that the needle is properly magnetized so as to be accurately tracked by the needle guidance system. In one embodiment a first key is included with the magnetizing system and configured to cooperatively mate with a second key included with the needle of the medical device. Various types of keys are disclosed herein.

As mentioned, the needle can be included as part of a medical device, such as a catheter insertion tool as described further below, though many other implementations with other types of medical devices are contemplated.

Figure 1A:
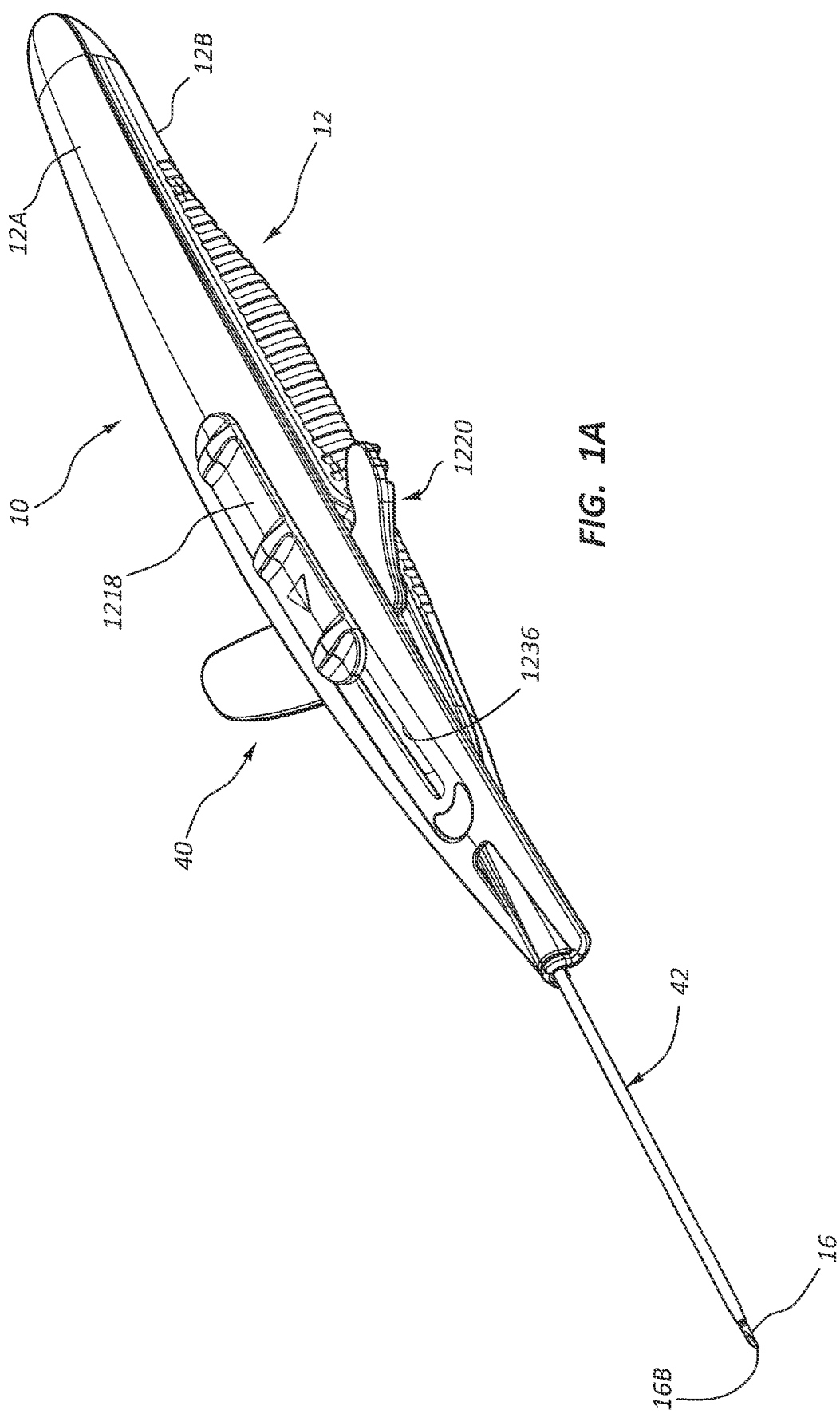
FIGS. 1A and 1B depict various views of a catheter insertion device according to one embodiment.
Figure 1B:
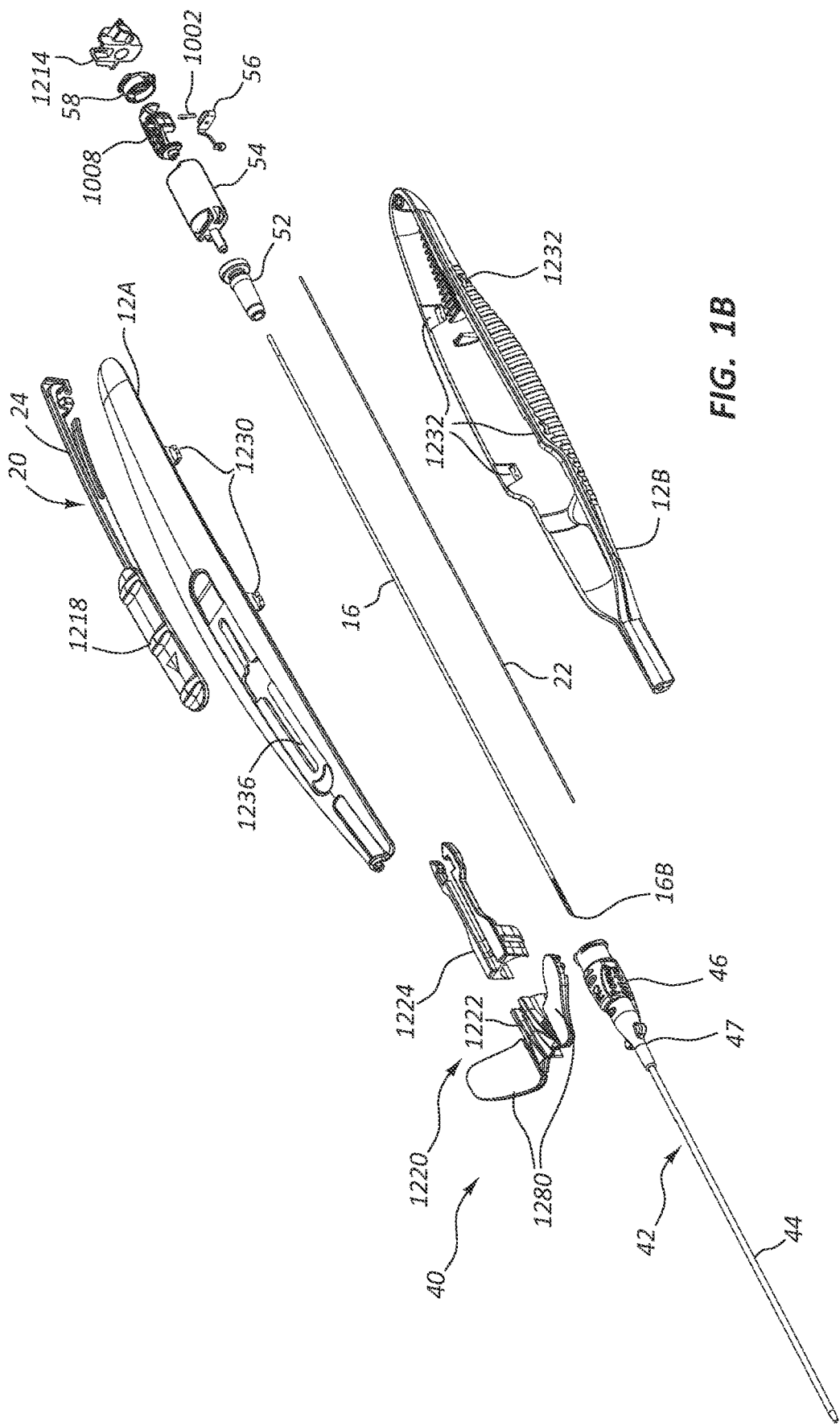

FIGS. 1A-1B depict various details of an insertion tool, or insertion device, 10 for assistance in inserting a catheter into a body of as patient, which also serves as an example of a medical device including a needle that can be magnetized with the present magnetizing system according to one embodiment. As shown in FIG. 1A, the insertion tool 10 includes top and bottom housing portions 12A, 12B of a housing 12, from which extends a catheter 42 disposed over a needle 16. Also shown is a finger pad 1218 of a guidewire advancement assembly 20 slidably disposed in a slot 1236 defined in the top housing portion 12A, and a portion of a handle assembly 1220 of a catheter advancement assembly 40. Further details are given below of the present insertion tool 10 and its various details in accordance with the present embodiment.

FIGS. 1A-1B show that the finger pad 1218 as part of the guidewire advancement assembly 20 can be slid by a finger(s) of the user distally along the slot 1236 in order to enable selective advancement of a guidewire 22 (initially disposed within a lumen of the needle 16) out past a distal end 16B of the needle 16. A proximal end of the guidewire 22 is attached to an interior portion of the top housing portion 12A such that a single unit of distal sliding advancement of the finger pad 1218 results in two units of distal guidewire advancement. This is made possible by looping the guidewire 22 from its attachment point on the top housing portion 12A and through guide surfaces included on the guidewire lever 24 before extending into the lumen of the needle 16. Note that in the present embodiment the guidewire lever 24 and finger pad 1218 of the guidewire advancement assembly 20 are integrally formed with one another, though they may be separately formed in other embodiments. Note also that the guidewire 22 can be attached to other external or internal portions of the insertion tool 10, including the bottom housing portion 12B, the needle hub 1214, etc.

FIGS. 1A and 1B further show that the catheter advancement assembly 40 for selectively advancing the catheter 42 in a distal direction out from the housing 12 of the insertion tool 10 includes a handle assembly 1220, which in turn includes among other components two wings 1280 that are grasped by the fingers of the user when the catheter is to be advanced. The wings 1280 distally advance via the gap 1250 defined between the top and bottom housing portions 12A, 12B.

The top and bottom housing portions 12A, 12B are mated together via the engagement of four tabs 1230 of the top housing portion with four corresponding recesses 1232 located on the bottom housing portion. Of course, other mating mechanisms and schemes can be employed for joining the top and bottom housing portions together.

The exploded view of the insertion tool 10 in FIG. 1B shows that the handle assembly 1220 includes a head portion 1222 from which extend the wings 1280, and a tail portion 1224. Both the head portion 1222 and the tail portion 1224 are removably attached to the catheter hub 46. Internal components of the insertion tool 10 that are disposed within the housing 12, each of which is passed through by the needle 16 include a valve 52, a safety housing 54 in which a carriage 1008 and a needle safety component 56 is disposed, and a cap 58 of the safety housing. An O-ring 1002 that is included with the needle safety component 56 is also shown, as is a needle hub 1214, which is secured to a proximal end of the needle 16 and is mounted to the housing 12 to secure the needle 16 in place within the insertion tool 10. Note in FIG. 1B that, in one embodiment, the slot 1236 in which the finger pad of the guidewire advancement assembly 20 is disposed includes a relatively wide portion to enable the guidewire lever 24 to be inserted therethrough in order to couple the guidewire advancement assembly to the housing 12.

The insertion tool 10 is used by a clinician to insert the catheter 42 into the venous system (or other location) of a patient so as to enable fluids, medicaments, etc. to be infused into and/or removed from the patient. Though depicted here as a midline catheter, the catheter 42 can include a catheter of a variety of lengths, including relatively shorter peripheral catheters, peripherally inserted central catheters, CVCs, etc. Also, other elongate medical devices can be employed as benefit from the present disclosure, including solid and hollow needles and cannulae, blood-draw needles, biopsy needles, introducer needles, guidewires, stylets, tissue-penetrating medical components, etc. Further details regarding the insertion tool 10 and its operation can be found in U.S. Pat. No. 9,950,139, titled "Catheter Placement Device Including Guidewire and Catheter Control Elements," which is incorporated by reference in its entirety into this application.

Figure 15:
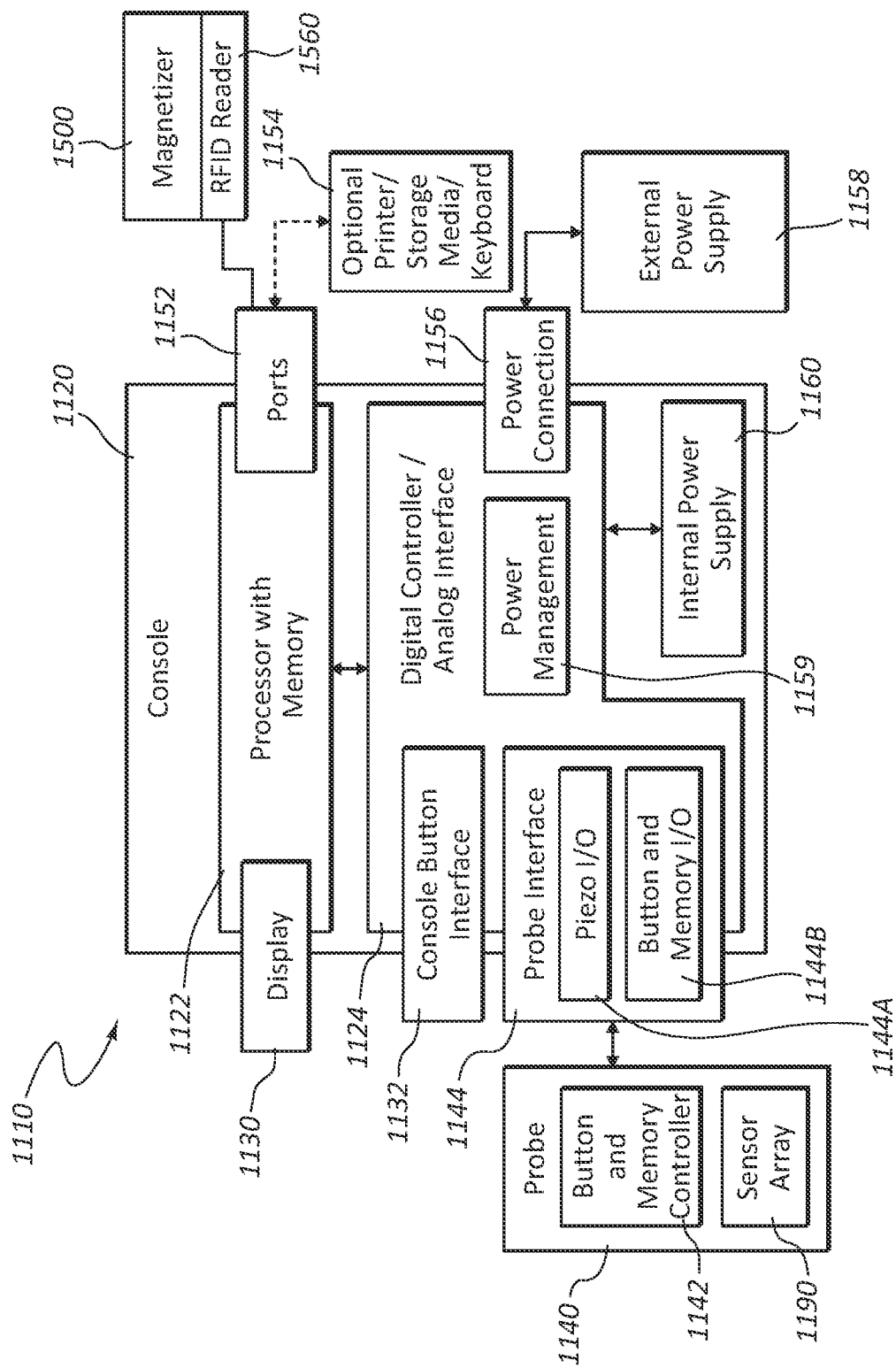
FIG. 15 is a block diagram of a guidance system for a medical device.
Figure 16:
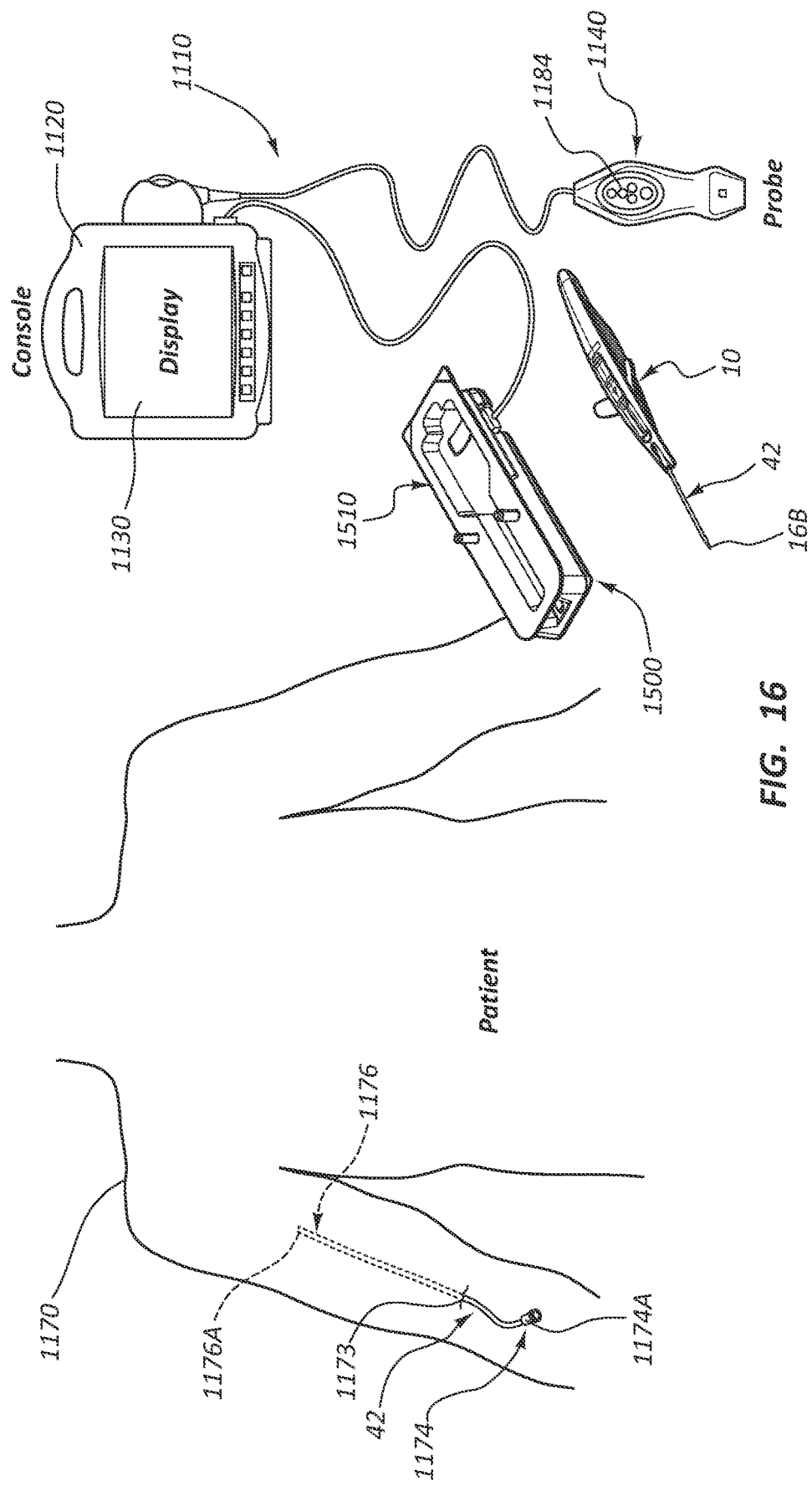
FIG. 16 is a simplified view of a guidance system for use in inserting a catheter assembly into a patient.

FIGS. 15 and 16 depict various aspects of a ultrasound-based guidance system ("system"), generally designated at 1110, which serves as one example environment wherein principles of the embodiments described herein can be practiced, including the insertion of the catheter 42 using the insertion tool 10 shown in FIGS. 1A and 1B as described further above.

In greater detail, the guidance system 1110 is configured for locating and guiding a needle or other medical component, during ultrasound-based or other suitable procedures, in order to access a subcutaneous vessel of a patient, for instance. In one embodiment, the guidance system enables the position, orientation, and advancement of the needle to be superimposed in real-time atop the ultrasound image of the vessel, thus enabling a clinician to accurately guide the needle to the intended target. Furthermore, in one embodiment, the guidance system tracks the needle's position in five degrees of motion: X, Y, and Z spatial coordinate space, needle pitch, and needle yaw. Such tracking enables the needle to be guided and placed with relatively high accuracy.

As shown in FIGS. 15 and 16, the system 1110 generally includes an ultrasound ("US") imaging portion including a console 1120, display 1130, and probe 1140, each of which is described in further detail below. It should be noted, however, that the ultrasound imaging portion can be configured in one of a variety of ways in addition to what is shown and described herein.

The ultrasound imaging portion of the system 1110 is employed to image a targeted internal portion of a body of a patient prior to percutaneous insertion of a needle or other device to access the target. As described below, in one embodiment insertion of the needle is performed prior to the subsequent insertion of a catheter into a vein or other portion of the vasculature of the patient. It is appreciated, however, that insertion of a needle into the body of a patient can be performed for a variety of medical purposes in addition to catheter insertion.

FIG. 16 shows the general relation of the above-described components to a patient 1170 during a procedure to ultimately place the catheter 42 (see FIGS. 1A and 1B) into the patient vasculature through a skin insertion site 1173, according to one embodiment. FIG. 16 shows that the catheter 42 generally includes a proximal portion 1174 that remains exterior to the patient and a distal potion 1176 that resides within the patient vasculature after placement is complete. The system 1110 is employed to ultimately position a distal tip 1176A of the catheter 42 in a desired position within the patient vasculature.

The catheter proximal portion 1174 further includes a luer connector 1174A configured to operably connect the catheter 42 with an infusion apparatus. As mentioned, placement of a needle into the patient vasculature at the insertion site 1173 is typically performed prior to insertion of the catheter, though it is appreciated that other placement methods can be employed. Further, it is appreciated that the above discussion is only one example for use of the system 1110; indeed it can be employed for a variety of uses, such as the placement of needles preparatory to insertion of a catheter as above, the insertion of a needle for other uses, or for the insertion of other medical components into the body of a patient, including x-ray or ultrasound markers, biopsy sheaths, ablation components, bladder scanning components, vena cava filters, etc.

The console 1120 houses a variety of components of the system 1110 and it is appreciated that the console can take one of a variety of forms. A processor 1122, including non-volatile memory such as EEPROM for instance, is included in the console 1120 for controlling system function and executing various algorithms during operation of the system 1110, thus acting as a control processor. A digital controller/analog interface 1124 is also included with the console 1120 and is in communication with both the processor 1122 and other system components to govern interfacing between the probe 1140 and other system components.

The system 1110 further includes ports 1152 for connection with additional components such as optional components 1154 including a printer, storage media, keyboard, etc. The ports in one embodiment are USB ports, though other port types or a combination of port types can be used for this and the other interfaces connections described herein. A power connection 1156 is included with the console 1120 to enable operable connection to an external power supply 1158. An internal battery 1160 can also be employed, either with or exclusive of an external power supply. Power management circuitry 1159 is included with the digital controller/analog interface 1124 of the console to regulate power use and distribution.

The display 1130 in the present embodiment is integrated into the console 1120 and is used to display information to the clinician during the placement procedure, such as an ultrasound image of the targeted internal body portion attained by the probe 1140. In another embodiment, the display may be separate from the console. In one embodiment, a console button interface 1132 and control buttons 1184 (FIG. 16) included on the probe 1140 can be used to immediately call up a desired mode to the display 1130 by the clinician to assist in the placement procedure. In one embodiment, the display 1130 is an LCD device.

FIG. 16 further depicts a needle-based device, namely, the insertion device 10 depicted in FIGS. 1A and 1B, used to gain initial access to the patient vasculature via the insertion site 1173 and to deploy the catheter 42 into the patient 1170. As will be described in further detail below, the needle 16 of the insertion device 10 is configured to cooperate with the system 1110 in enabling the system to detect the position, orientation, and advancement of the needle during an ultrasound-based placement procedure.

FIGS. 15 and 16 also show that the system 1110 includes a magnetizer 1500, described in greater detail further below, configured to magnetize all or a portion of the needle 16 of the insertion device 10 so as to enable the needle to tracked during the catheter placement procedure. The magnetizer 1500 includes in the present embodiment an RFID reader 1560 to enable it to read RFID tags included with the insertion device 10, which enables the system 1110, among other things, to customize its operation to the particular size and type of needle included with the insertion device. More details regarding the RFID reader 1560 are given further below.

The probe 1140 is employed in connection with ultrasound-based visualization of a vessel, such as a vein, in preparation for insertion of the needle 16 and/or catheter 42 into the vasculature. Such visualization gives real time ultrasound guidance and assists in reducing complications typically associated with such introduction, including inadvertent arterial puncture, hematoma, pneumothorax, etc.

The handheld probe 1140 includes a head 1180 that houses a piezoelectric array for producing ultrasonic pulses and for receiving echoes thereof after reflection by the patient's body when the head is placed against the patient's skin proximate the prospective insertion site 1173 (FIG. 16). The probe 1140 further includes a plurality of control buttons 1184 (FIG. 16) for controlling the system, thus eliminating the need for the clinician to reach out of the sterile field, which is established about the patient insertion site prior to establishment of the insertion site, to control the system 1110.

As such, in one embodiment a clinician employs the ultrasound imaging portion of the system 1110 to determine a suitable insertion site and establish vascular access, such as with the insertion tool needle 16, prior to introduction of the catheter 42 (also included on the insertion tool) for ultimate advancement thereof through the vasculature toward an intended destination.

FIG. 15 shows that the probe 1140 further includes a button and memory controller 1142 for governing button and probe operation. The button and memory controller 1142 can include non-volatile memory, such as EEPROM, in one embodiment. The button and memory controller 1142 is in operable communication with a probe interface 1144 of the console 1120, which includes a piezo input/output component 1144A for interfacing with the probe piezoelectric array and a button and memory input/output component 1144B for interfacing with the button and memory controller 1142.

Also as seen in FIG. 15, the probe 1140 includes a sensor array 1190 for detecting the position, orientation, and movement of the insertion tool needle 16 during ultrasound imaging procedures, such as those described above. In the present embodiment, the sensor array 1190 includes a plurality of magnetic sensors 1192 embedded within or included on the housing of the probe. The sensors 1192 are configured to detect a magnetic field associated with the needle 16 when it is magnetized and thus enable the system 1110 to track the needle. Though configured here as magnetic sensors, it is appreciated that the sensors 1192 can be sensors of other types and configurations, as will be described. Also, though they are described herein as included with the probe 1140, the sensors 1192 of the sensor array 1190 can be included in a component separate from the probe, such as a separate handheld device, in one embodiment. In one embodiment, the sensors 1192 are disposed in an annular configuration about the head portion of the probe 1140, though it is appreciated that the sensors can be arranged in other configurations, such as in an arched, planar, or semi-circular arrangement.

In the present embodiment, each of the sensors 1192 includes three orthogonal sensor coils for enabling detection of a magnetic field in three spatial dimensions. Such three dimensional ("3-D") magnetic sensors can be purchased, for example, from Honeywell Sensing and Control of Morristown, NJ Further, the sensors 1192 of the present embodiment are configured as Hall-effect sensors, though other types of magnetic sensors could be employed. Further, instead of 3-D sensors, a plurality of one dimensional magnetic sensors can be included and arranged as desired to achieve 1-, 2-, or 3-D detection capability.

In the present embodiment, five sensors 1192 are included in the sensor array 1190 so as to enable detection of the needle 1200 in not only the three spatial dimensions (i.e., X, Y, Z coordinate space), but also the pitch and yaw orientation of the needle itself. Note that in one embodiment, orthogonal sensing components of two or more of the sensors 1192 enable the pitch and yaw attitude of the needle 16 to be determined.

In other embodiments, fewer or more sensors can be employed in the sensor array. More generally, it is appreciated that the number, size, type, and placement of the sensors of the sensor array can vary from what is explicitly shown here.

It is appreciated that the needle 16 is composed of a magnetizable material to enable the needle to be magnetized by the below-described magnetizer and later be tracked by the guidance system 1110 when the needle is percutaneously inserted into the body of the patient 1170 during a procedure to insert the needle or an associated medical device into the body of the patient. In one embodiment, the needle 16 is composed of a stainless steel, such as SS 304 stainless steel, though other suitable needle materials that are capable of being magnetized can be employed. In one embodiment, the needle material is ferromagnetic. In another embodiment, the needle is paramagnetic. So configured, the needle 16 produces a magnetic field that is detectable by the sensor array 1190 of the ultrasound probe 1140 so as to enable the location, orientation, and movement of the needle 16 to be tracked by the system 1110, as described further below.

During operation of the system 1110, the head portion of the ultrasound probe 1140 is placed against the patient skin and produces an ultrasound beam so as to ultrasonically image a portion of a vessel beneath the patient skin surface. The ultrasonic image of the vessel can be depicted on the display 1130 of the system 1110 (FIGS. 15, 16).

As mentioned above, the system 1110 in the present embodiment is configured to detect the position, orientation, and movement of the needle 16 of the insertion device 10 described above. In particular, the sensor array 1190 of the probe 1140 is configured to detect a magnetic field of the magnetized needle 16. Each of the sensors 1192 of the sensor array 1190 is configured to spatially detect the magnetized needle in three dimensional space. Thus during operation of the system 1110, magnetic field strength data of the needle's magnetic field sensed by each of the sensors 1192 is forwarded to a processor, such as the processor 1122 of the console 1120 (FIG. 15), which computes in real-time the position and/or orientation of the needle 16.

In light of the above, the position of the entire length of the needle 16 in X, Y, and Z coordinate space with respect to the sensor array 1190 can be determined by the system 1110 using the magnetic field strength data sensed by the sensors 1192. Moreover, the pitch and yaw of the needle 16 can also be determined. Suitable circuitry of the probe 1140, the console 1120, or other component of the system can provide the calculations necessary for such position/orientation. In one embodiment, the magnetic element 210 can be tracked using the teachings of one or more of the following U.S. Pat. Nos. 5,775,322; 5,879,297; 6,129,668; 6,216,028; and 6,263,230, each of which is incorporated by reference in its entirety into this application.

The above position and orientation information determined by the system 1110, together with the length of the needle 16, as known by or input into the system, enable the system to accurately determine the location and orientation of the entire length of the needle, including its distal tip 16B, with respect to the sensor array 1190. This in turn enables the system 1110 to superimpose an image of the needle 16 on to an image produced by the ultrasound beam 1222 of the probe 1140, such as via a screenshot depicted on the display 1130 (FIGS. 15, 16), for instance. For example, the ultrasound image depicted on the display 1130 can include depiction of the patient skin surface and a subcutaneous vessel to be accessed by the needle 16, as well as a depiction of the needle 16 as detected by the system 1110 and its position with respect to the vessel. The ultrasound image corresponds to an image acquired by the ultrasound beam of the probe 1140. In another embodiment, it is appreciated that only a portion of the length of the needle 16 is magnetized and thus tracked by the guidance system.

Note that further details regarding structure and operation of the above-described guidance system can be found in U.S. Pat. No. 9,456,766, titled "Apparatus for Use with Needle Insertion Guidance System," which is incorporated by reference in its entirety into this application.

As mentioned above, in the present embodiment the needle 16 of the insertion tool 10 is magnetized so as to be trackable by the guidance system 1110 when the needle is inserted into the body of the patient. Such magnetic-based tracking of the needle 16 assists the clinician in placing the distal tip 16B of the needle in a desired location, such as in the lumen of a vein, by superimposing a simulated needle image representing the real-time position and orientation of the needle over an ultrasound image of the internal area of the patient body being accessed by the needle.

Embodiments described below provide apparatus and systems for magnetizing a needle, such as the needle 16 shown in FIGS. 1A and 1B, including needles and cannulae from a variety of medical devices, including needles themselves as the medical device. Thus, though dealing with magnetization of the needle 16 of the insertion tool 10 (FIGS. 1A and 1B), the following discussion should not be considered as limiting.

Figure 2D:
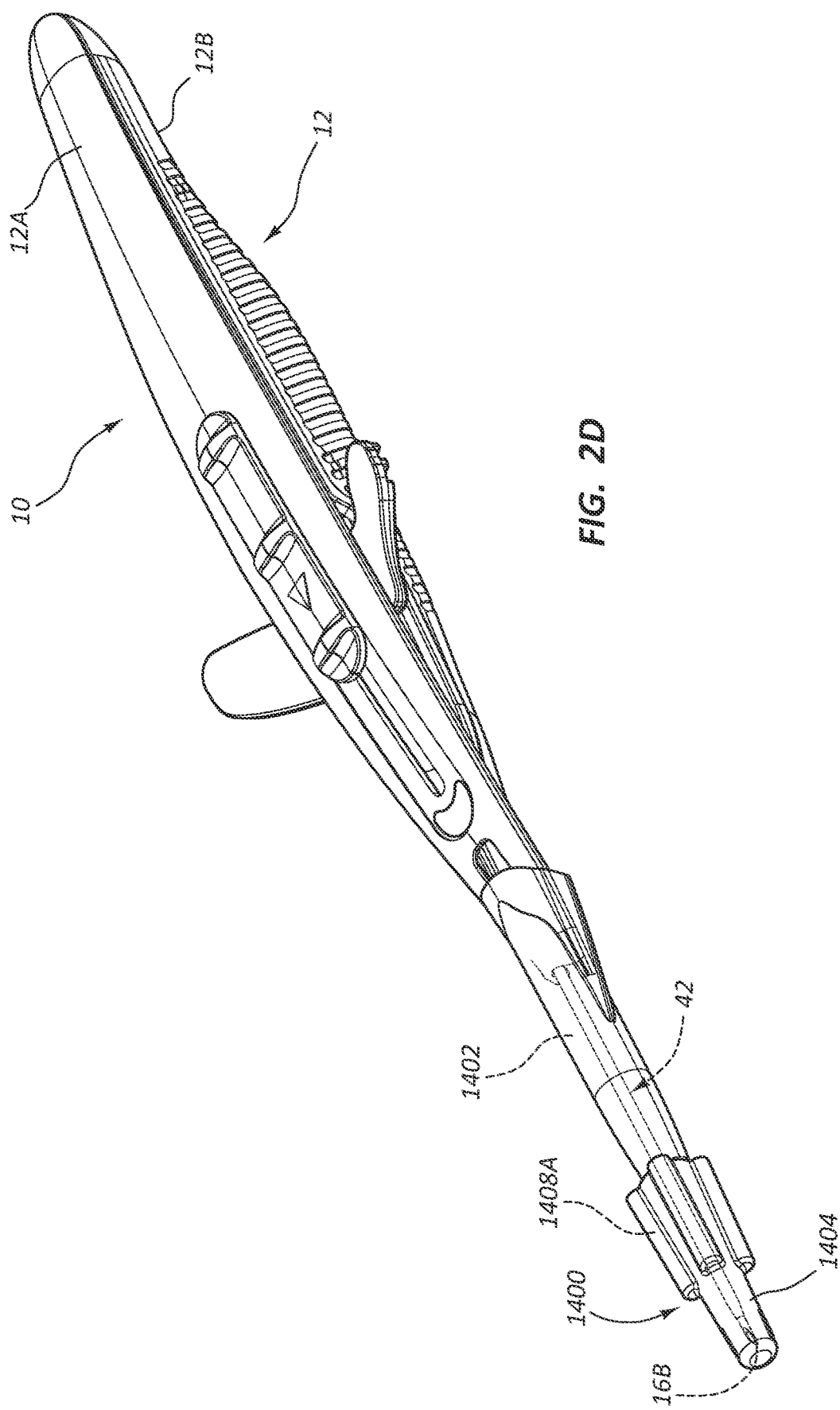

FIGS. 2A-2D depict one example of an apparatus for magnetizing the needle 16 of the insertion tool 10 (FIGS. 1A, 1B) according to one embodiment. As shown, a needle cover 1400 is included, which is configured to fit on to and removably attach to the insertion tool 10 so as to cover the portion of the needle 16 and the catheter 42 that distally extend from the insertion tool housing 12. The needle cover 1400 defines a cavity 1402 for receiving the needle 16 and catheter 42 therein and is sized as to removably engage with the distal portion of the housing 12 so as to protect the user from accidental needle sticks before use of the insertion tool 10, as shown in FIG. 2D.

A cap 1404 is permanently attached (such as via adhesive) to a distal end of the needle cover 1400 and includes four slots 1406 equally spaced apart about the outer perimeter of the cap. Within each slot 1406 is disposed a magnetic element, such as a permanent magnet 1408. In the present embodiment, the permanent magnets 1408 are configured as bar magnets 1408A sized to be permanently received within the slots 1406 and held in place by an adhesive or other suitable mode. The poles of the permanent magnets 1408 are aligned so as to correspond with the other magnets.

When the needle cover 1400 is mated with the insertion tool 10 such that the distal portion of the needle 16 is disposed within the cavity 1402 thereof (FIG. 2D), the magnets 1408 disposed within the corresponding slots 1406 are positioned proximate the distal portion of the needle. The needle cover is placed over the needle 16 in this manner after manufacture and remains in place during packaging, transport and storage until the insertion tool is accessed to be used by a clinician.

The proximate positioning of the magnets 1408 to the needle 16 immediately magnetizes the distal portion of the needle. In one embodiment, the magnets 1408 each have a longitudinal length of about 1 inch, sufficient to magnetize the distal portion of the needle 16. It is appreciated, though, that other numbers, sizes, lengths, and magnetization lengths of the magnets and the needle are possible in other embodiments. For instance, three relatively shorter magnets could be included on the cap 1404 in one embodiment. It is further appreciated that, though the permanent magnets 1408 in the present embodiment are dipole magnets, in other embodiments each slot 1406 could hold a plurality of magnets stacked end to end to form a multipole magnet arrangement. The permanent magnets 1408 in one embodiment are rare-earth magnets such as neodymium magnets, though other suitable magnetic materials could be employed. These and other configurations are contemplated.

FIGS. 3A-3C depict details of the needle cover 1400 according to another embodiment, wherein the cap 1404 is omitted and the permanent magnet 1408 includes a single permanent, annular magnet 1408B, which is slid over the external surface of the needle cover so as to be disposed proximate the distal portion of the needle 16 residing on the needle cover cavity 1402 when the needle cover is mated with the insertion tool 10, similar to that shown in FIG. 2D. In this way, the needle 16 is magnetized by the annular magnet 1408B of FIGS. 3A-3C when the needle cover 1400 is in place, thus enabling the needle to be tracked by a suitable needle tracking system.

Figure 5:
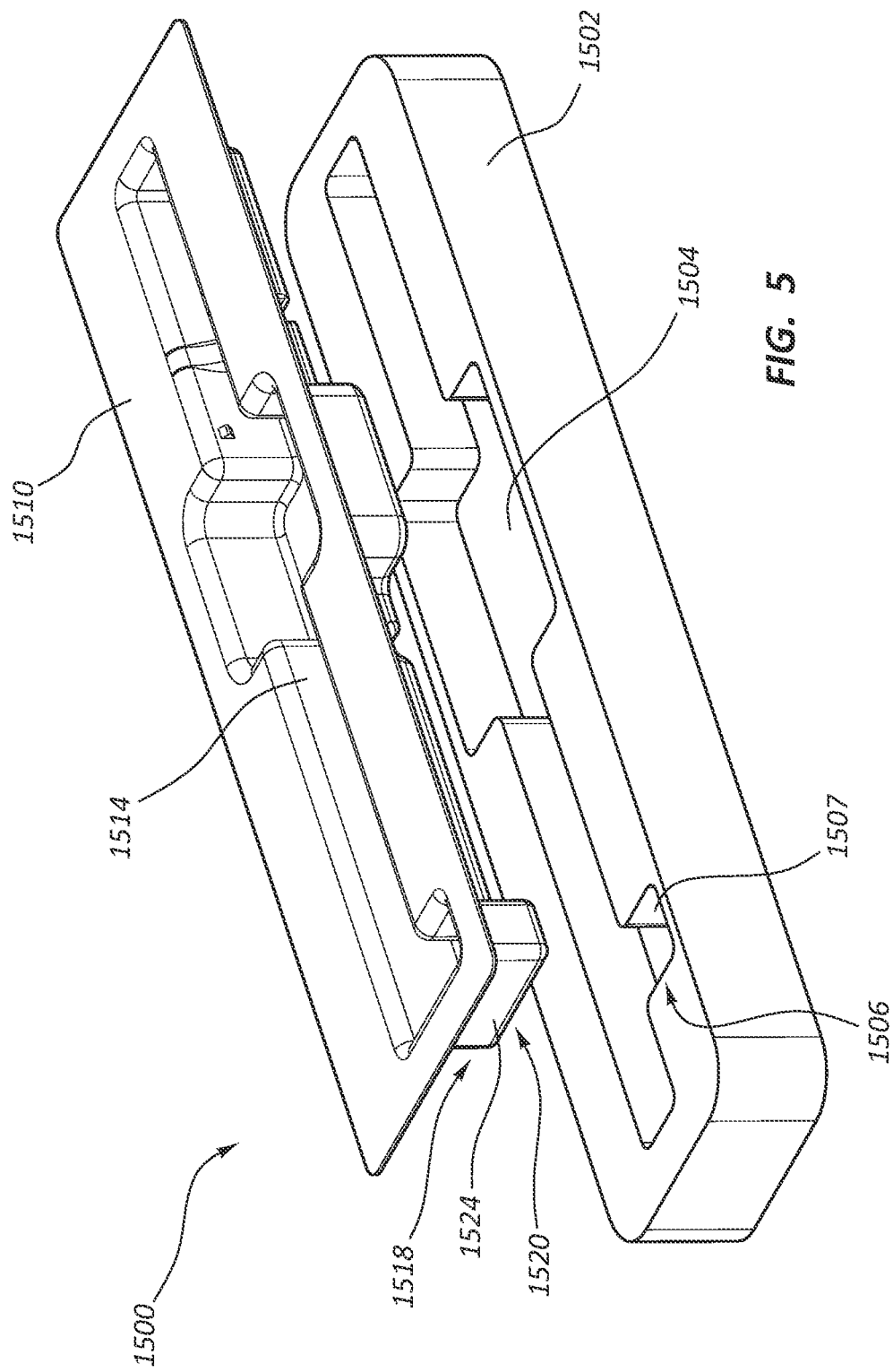
FIG. 5 is a perspective view of a magnetizer and tray assembly according to one embodiment.

FIGS. 4A-4C depict details of the needle cover 1400 according to another embodiment, wherein a key feature 1420 is included therewith. The key feature 1420 assists with positioning the needle 16 in a desired position and orientation with respect to a magnetizer (for magnetizing the needle) when the needle cover 1400 is mated to the insertion tool 10 (similar to that shown in FIG. 2D) and the insertion tool is placed on or proximate to the magnetizer. An example of a similar magnetizer is shown in FIG. 5, for instance. In brief, the magnetizer is configured to immediately magnetize a predetermined segment of the distal portion of the needle 16 of the insertion tool 10 (FIGS. 1A and 1B) when the insertion tool is placed on/proximate the magnetizer. To that end, the magnetizer includes one or more permanent magnets that are disposed and arranged to magnetize the needle when the needle 16 is positioned as discussed herein. For instance, in the present embodiment, five permanent magnets are located in the magnetizer and placed end-to-end in a multipole arrangement. This results in a multipole magnetization profile imparted to the distal portion of the needle 16, which multipole profile can be then be detected and tracked by the guidance system 1110 discussed above. Note that the multipole magnet arrangement assists in providing a robust magnetization to the needle 16, rendering other residual magnetic fields that may be present on the needle unproblematic. It is appreciated that other magnetic sources, such as an electromagnet, can be employed to magnetize the needle, in other embodiments. As such, the embodiments described herein are not meant to be limiting.

In the present embodiment, the magnetizer comprises part of the guidance system 1110, though in other embodiments it can be a separate component.

In further detail, the key feature 1420 of the cover 1400 of FIGS. 4A-4C is configured to fit with a corresponding key structure on or associated with the magnetizer so that the needle 16 is placed in the desired position and orientation on the magnetizer. Thus, an orientation key system is established, with corresponding keys included on the needle cover 1400 and the magnetizer. Upon being properly placed on the magnetizer, the distal portion of the needle 16 can then be magnetized by the multipole magnet arrangement described above.

In the present embodiment and as seen in FIGS. 4A-4C, the key feature 1420 in the present embodiment includes a fin 1424 extending from a bottom surface 1400B of the needle cover 1400. A corresponding slot can be included in the body of the magnetizer to receive the fin 1424, which causes the needle cover 1400 and attached insertion tool 10 to be placed on the magnetizer in a specified, desired orientation. In turn, this causes the distal portion of the needle 16, disposed within the needle cover 1400, to be placed in sufficient proximity, and in the proper desired orientation, to the set of magnets in the magnetizer so as to be magnetized thereby. Once magnetization occurs, which is substantially immediate, the insertion tool 10 can be removed from the magnetizer, the needle cover removed, and the insertion tool used to insert the needle and catheter into the body of the patient.

FIGS. 5-8C depict various details of a magnetizing system according to one embodiment, including a magnetizer 1500 and a tray 1510 that is removably matable with the magnetizer. As shown in FIGS. 5-6C, the magnetizer includes a body 1502 that defines a receptacle 1504 below which a plurality of permanent magnets 1508 are linearly disposed in a multipole arrangement (FIG. 6B). Note that the one or more magnets could be arranged in other than a linear arrangement within the magnetizer, in other embodiments.

A first key feature 1506 of an orientation key system 1518 is included with the magnetizer body 1502. In particular, the first key feature 1506 includes a recess 1507 that is defined by a portion of the receptacle 1504 and is sized to receive therein a corresponding key feature 1520 of the tray 1510. The tray 1510, which includes a receptacle 1514, includes a protrusion 1524 on a bottom surface thereof that serves as the second key feature 1520. The tray receptacle 1514 is sized to be received within the receptacle 1504 of the magnetizer body 1502. Correspondingly, the tray receptacle 1514 is sized to receive therein the insertion tool 10 (or other suitable medical device) in a predetermined orientation. Further, the protrusion 1524 is received into the correspondingly shaped recess 1507 of the magnetizer receptacle 1504 such that the needle is positioned accurately with respect to the magnets 1508 when the insertion tool-laden tray 1510 is inserted into the receptacle 1504 of the magnetizer body 1502. Magnetization of the desired distal portion of the needle 16 of the insertion tool 10 (through the tray 1510) then immediately occurs.

It is thus seen that the first key feature 1506 (i.e., the recess 1507 of FIG. 5 in the present embodiment) and the second key feature 1520 (i.e., the protrusion 1524 in the present embodiment) cooperate to serve as an orientation key system to ensure correct positioning of the insertion tool 10 on the magnetizer 1500 and, specifically, correct positioning of the needle 16 with respect to the permanent magnets 1508 of the magnetizer. It is appreciated that the orientation key system can be configured in other ways as seen, for example, in the embodiments described further below.

Figure 7C:
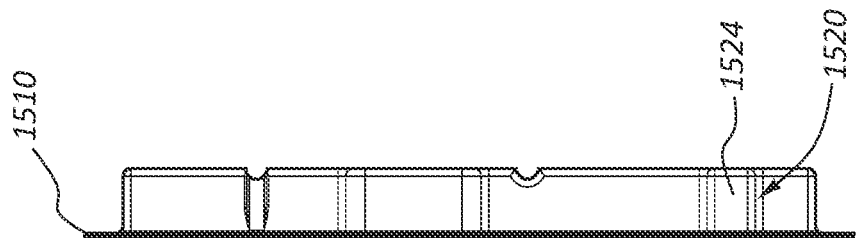
FIGS. 7A-7C depict various views of the tray of FIG. 5.
Figure 7B:
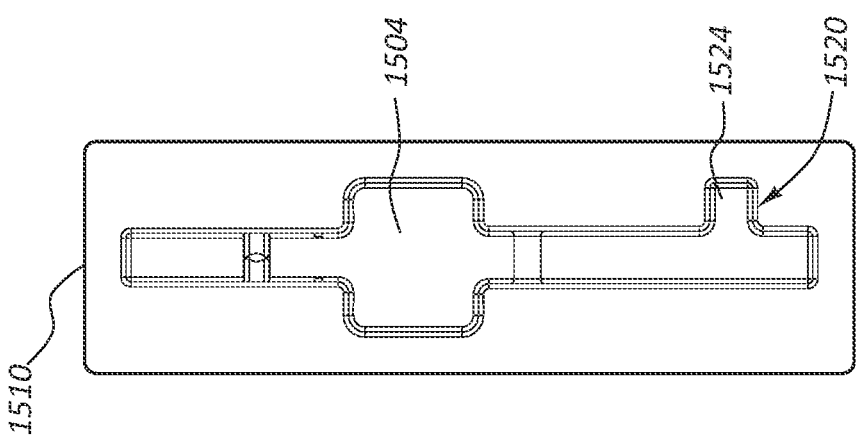
Figure 7A:
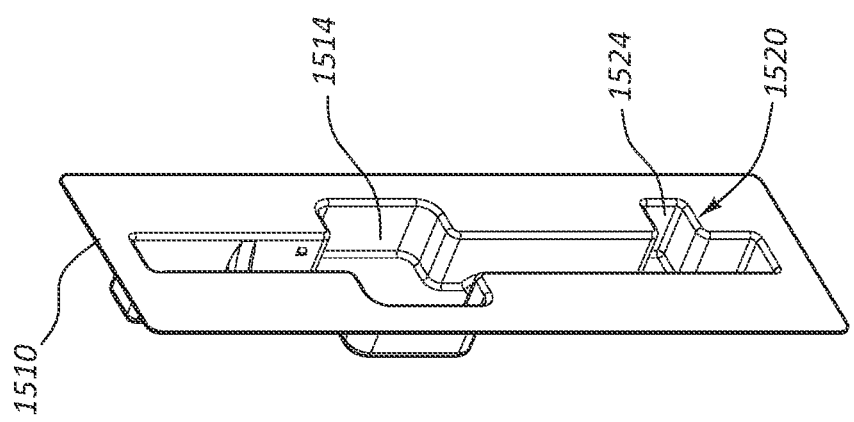
Figure 8C:
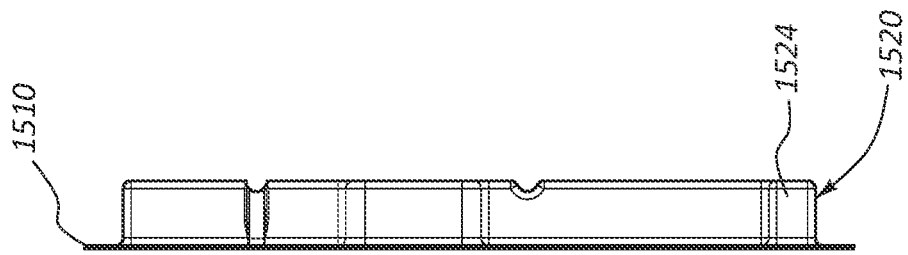
FIGS. 8A-8C depict various views of the tray of FIG. 5.
Figure 8B:
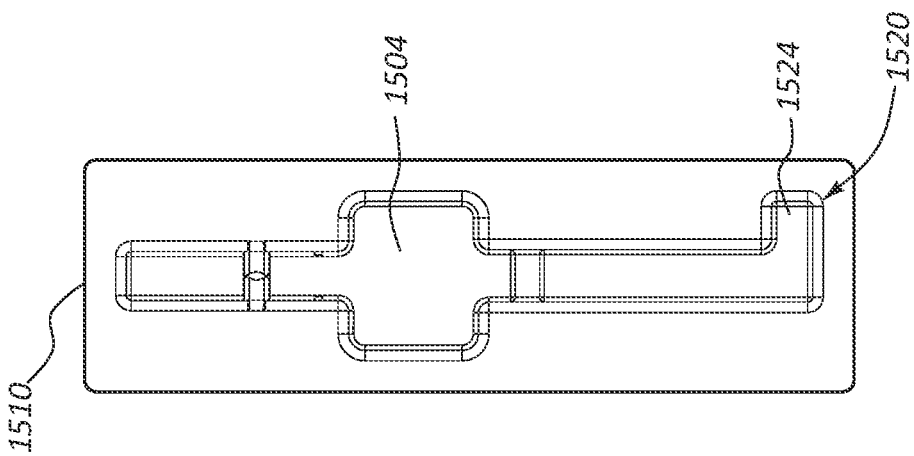
Figure 8A:
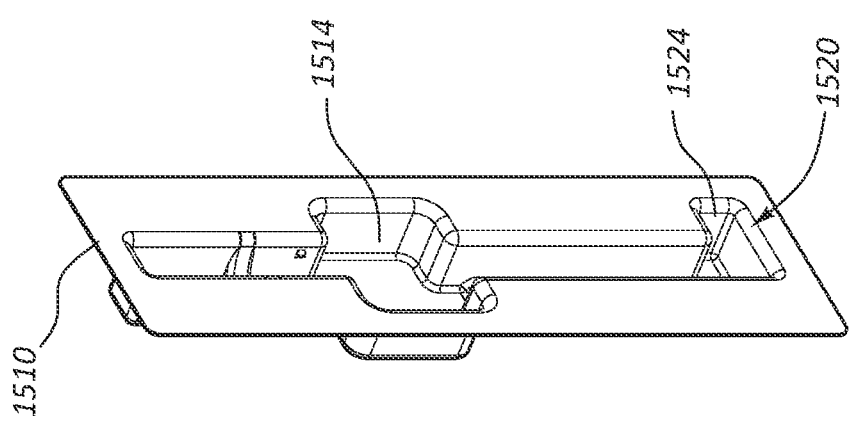

FIGS. 7A-7C show the tray 1510 configured to hold therein the insertion tool 10 including an 8 cm needle 16, while FIGS. 8A-8C show the tray configured to hold the insertion tool with a 10 cm needle. As such, the protrusion 1524 is positioned differently as part of the receptacle 1514 to accommodate the differently sized needle in each case. These and other variations are contemplated.

FIGS. 9A-11C depict various details of a magnetizing system including the magnetizer 1500 and the tray 1510, which is removably matable with the magnetizer, according to another embodiment. As shown, the magnetizer 1500 includes the body 1502 that defines the receptacle 1504. The receptacle 1504 in the present embodiment includes a relatively wide first portion 1504A that is slightly concavely shaped, and a narrowed second portion 1504B. The plurality of permanent magnets 1508 is linearly disposed within the magnetizer body 1502 in a multipole arrangement and disposed beneath the surface of the receptacle second portion 1504B, as best seen in FIG. 9C.

The tray 1510, which defines a receptacle 1514, is of a clamshell design in the present embodiment and thus includes a top portion 1510A and a bottom portion 1510B. The tray 1510 in the present embodiment includes PETG, though other polyethylene, thermoplastic, or suitable materials can be employed. As in the previous embodiment, the tray receptacle 1514 is sized to be removably received within the receptacle 1504 of the magnetizer. FIGS. 10A-10C (showing the magnetizer body 1502) and 11A-11C (showing the tray 1510) illustrate that the tray receptacle 1514 includes a relatively wider portion that is configured to be received into the first portion 1504A of the magnetizer receptacle 1504 and a relatively narrow portion that is configured to be received into the second portion 1504B of the magnetizer receptacle. Correspondingly, the tray receptacle 1514 is further sized to receive therein the insertion tool 10 in a predetermined orientation, as seen in FIGS. 9A-9C, such that the needle 16 is disposed in the narrow portion of the tray receptacle 1514, which correspondingly places the needle within the second portion 1504B of the magnetizer receptacle 1504 and adjacent the permanent magnets 1508, thus allowing the needle to be magnetized thereby when the tray is placed on the magnetizer body 1502.

The magnetizer 1500 and tray 1510 further include an orientation key system 1518 configured to ensure correct positioning of the insertion tool 10 on the magnetizer 1500 and, specifically, correct positioning of the needle 16 with respect to the permanent magnets 1508 of the magnetizer. In the present embodiment, the orientation key system 1518 includes a first key feature 1506, namely, a plurality of posts 1530 included on the magnetizer body 1502. As shown, two posts 1530 are included in an offset configuration and disposed on either side of the second portion 1504B of the receptacle 1504. Each post 1530 is sized differently in diameter from the other post.

Correspondingly, the orientation key system 1518 includes a second key feature 1520, included on the tray 1510, which is configured to cooperatively interact with the first key feature 1506 (i.e., the posts 1530 in the present embodiment) in order to satisfy the purpose of the orientation key system 1518, that is, to provide for the correct positioning of the insertion tool needle 16 with respect to the permanent magnets 1508. In the present embodiment, the second key feature 1520 includes two holes 1534 defined through both the top and bottom portions 1510A, 1510B of the tray 1510. The holes 1534 differ according to which tray portion they are defined through: a relatively larger, oblong hole 1534A is defined in two offset locations on the tray top portion 1510A, and a relatively smaller round hole 1534B is defined in two offset locations on the tray bottom portion 1510B so as to be aligned with the corresponding holes 1534A.

Figure 9A:
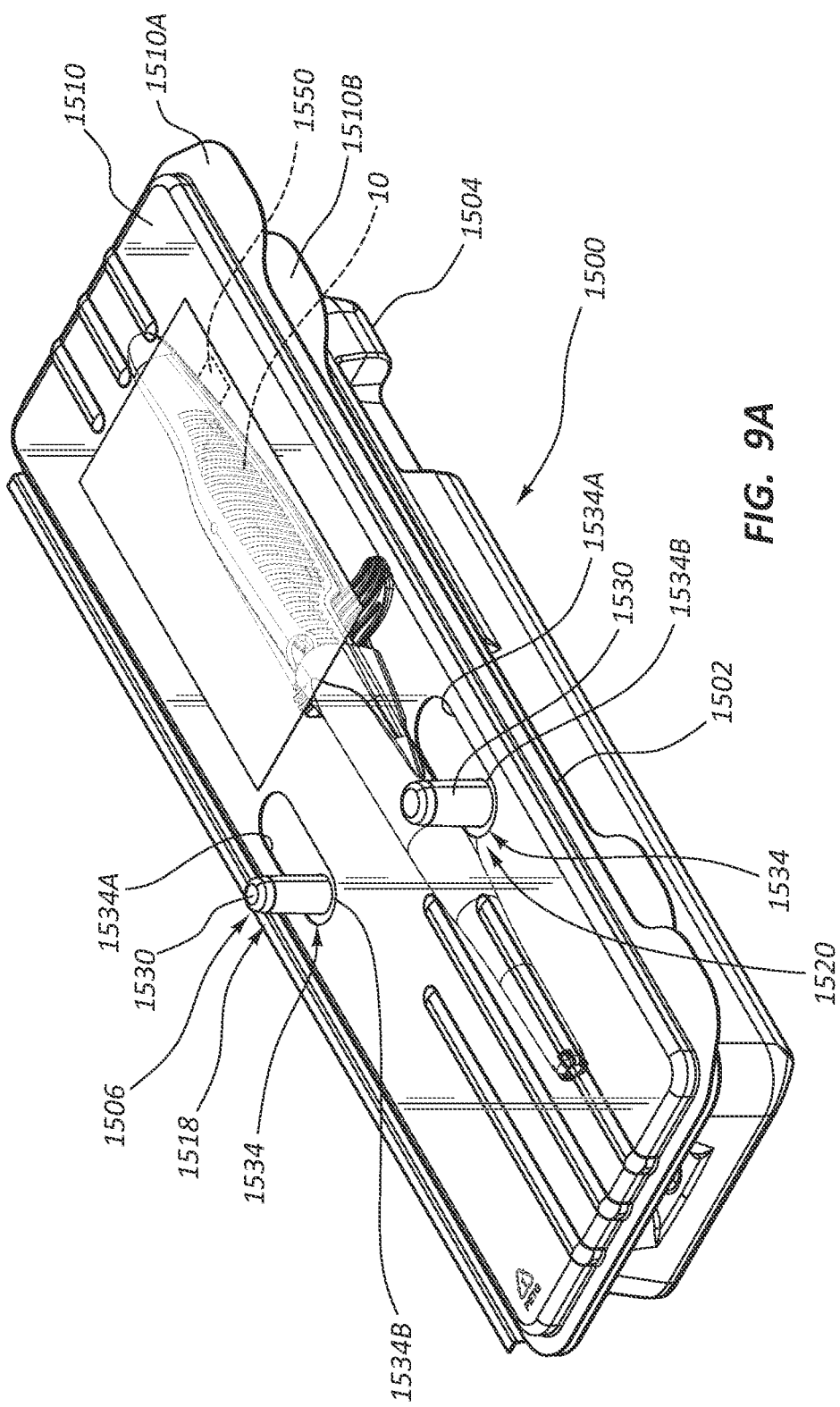
Figure 9B:
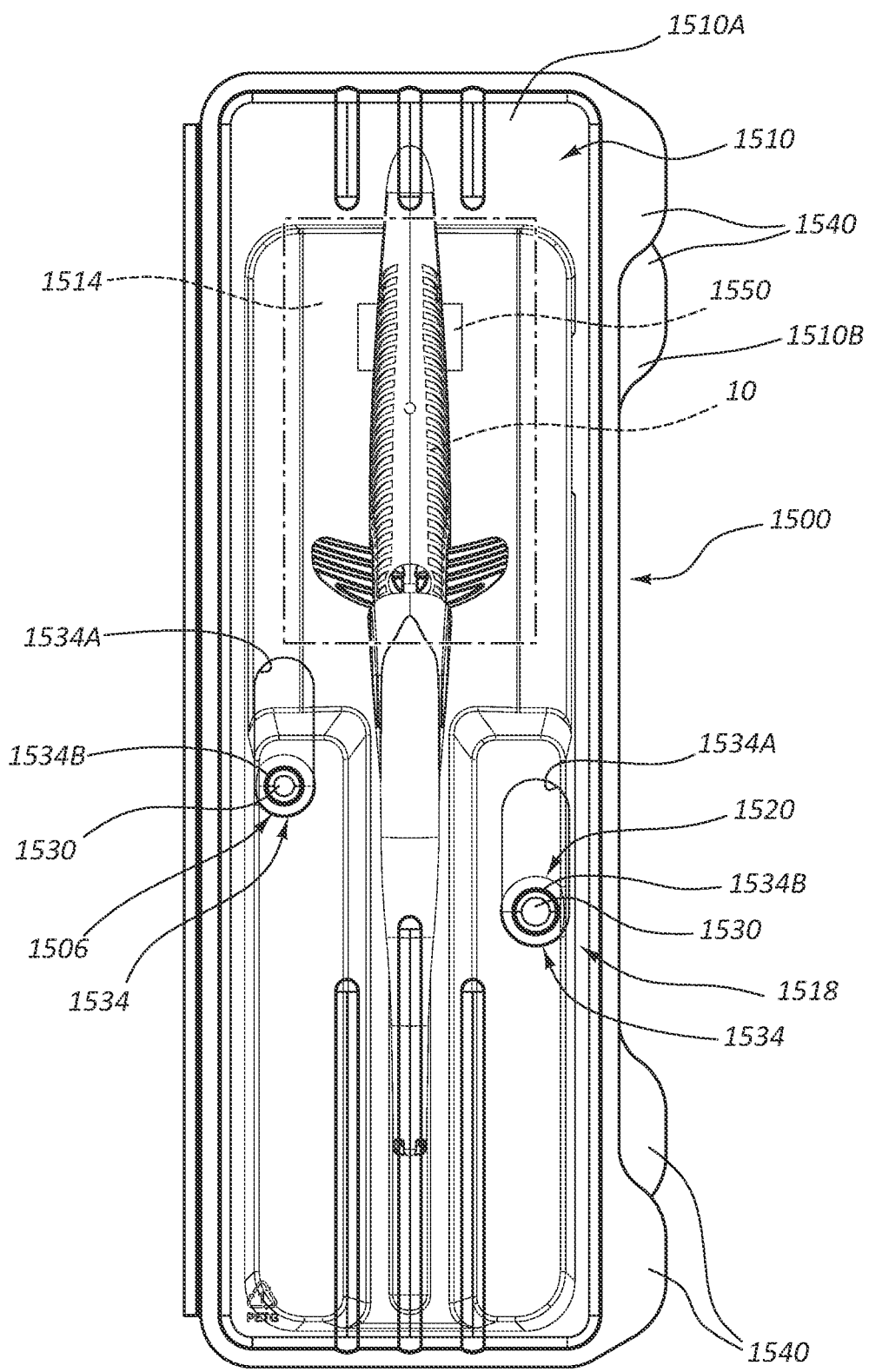
Figure 10C:
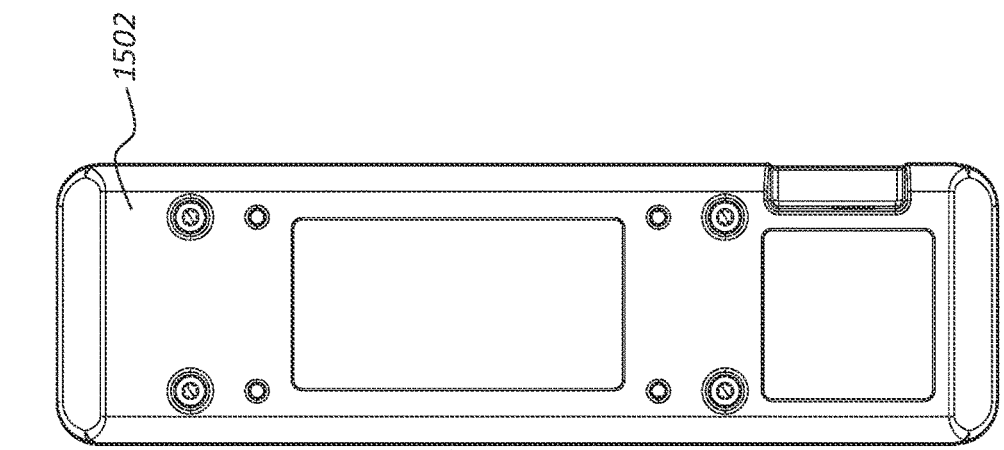
FIGS. 10A-10C depict various views of the magnetizer of FIGS. 9A-9C.
Figure 10B:
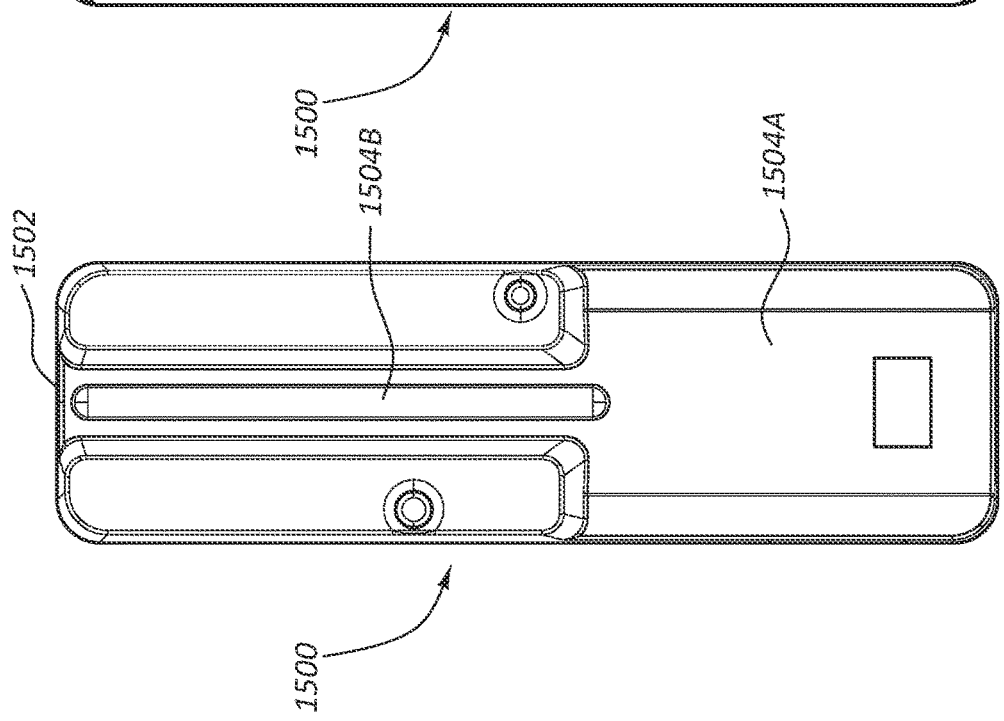
Figure 10A:
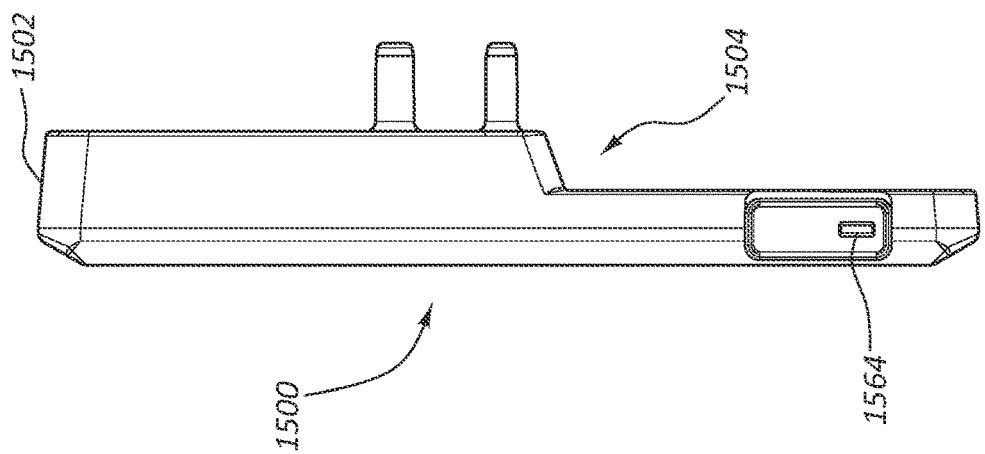

As best seen in FIG. 9A, the holes 1534 are received into the correspondingly positioned posts 1530 of the magnetizer body 1502 when the tray is placed on the magnetizer body 1502. In turn, this places the needle 16 of the insertion tool 10 (disposed in the tray 1510) in the second portion 1504B of the magnetizer receptacle 1504 and adjacent the permanent magnets 1508, thus allowing the needle to be magnetized thereby when the tray is placed on the magnetizer body 1502. In the present embodiment, the holes 1534 and the posts 1530 are positioned such that the distal tip 16B of the needle 16 is substantially co-terminal with the adjacent end-most permanent magnet 1508, as seen in FIG. 9C. This provides magnetization to the needle 16 beginning at the needle distal tip 16B and extending proximally therefrom, as is desired. In other embodiments, however, the holes, posts, and needle can be arranged in other positional configurations to provide a magnetization profile as may be desired.

Note that magnetization of the desired portion of the needle 16 substantially immediately occurs when the tray is placed on the magnetizer 1500. Thus, it is seen that the engagement of the tray holes 1534 (as the second key feature 1520) with the posts 1530 (as the first key feature 1506) of the magnetizer body 1502 ensures that the needle 16 is positioned properly with respect to the magnets, thus ensuring that magnetization of the desired portion of the needle is achieved. Again note that, though in the present embodiment, multipole magnetization of the distal portion of the needle 16 extends proximally along the needle beginning at the distal tip thereof, in other embodiments magnetization of other portions of the needle (or other magnetizable medical component) can be performed.

As mentioned, the posts 1530 are each differently sized in the present embodiment. In the present embodiment, the larger post 1530 has a diameter of about 0.363 inch while the relatively smaller posts has a diameter of about 0.300 inch, though other sizes are possible. The holes 1534B defined in the bottom portion 1510B of the tray 1510 are also correspondingly sized so as to mate with the posts 1530 in only one orientation, i.e., the orientation shown in FIGS. 9A-9C, which prevents misalignment of the needle 16 with the permanent magnets 1508.

Also, the posts 1530 in the present embodiment extend a predetermined height above the magnetizer body 1502, which forces a user, when removing the tray 1510 from the magnetizer after needle magnetization, to lift the tray vertically upward until the tray holes 1534 clear the posts, which direction is orthogonal to the longitudinal length of the plurality of permanent magnets 1508 included in the magnetizer body 1502 (FIG. 9C). This ensures that the needle 16 is withdrawn from proximity with the permanent magnets 1508 in a direction that will not re-write or distort the magnetic field on the needle imposed thereon by the magnets, as could be the case if the needle was slid laterally with respect to the permanent magnets at close distance. Note that the height of the posts can vary according to magnetic strength of the permanent magnets, etc. In the present embodiment, the posts are about 0.83 inch high, though other heights are also possible. Note also that the tray can be sterilized during time of manufacture/packaging such that, after magnetization of the insertion tool contained therein, the tray may be opened and the insertion tool dropped from the package into a sterile field of the patient, thus preserving the sterility of the insertion tool and the field.

Note that in the present embodiment, the magnetizer body receptacle 1504 and the tray receptacle 1514 are also configured such that the tray may be received into the magnetizer body receptacle in only one desired orientation. Thus, the configuration of the magnetizer body and tray receptacles 1504, 1514 serves as an additional key feature to ensure proper needle-to-magnet positioning and prevent backwards, upside-down, etc. positioning of the tray on the magnetizer.

Figure 12:
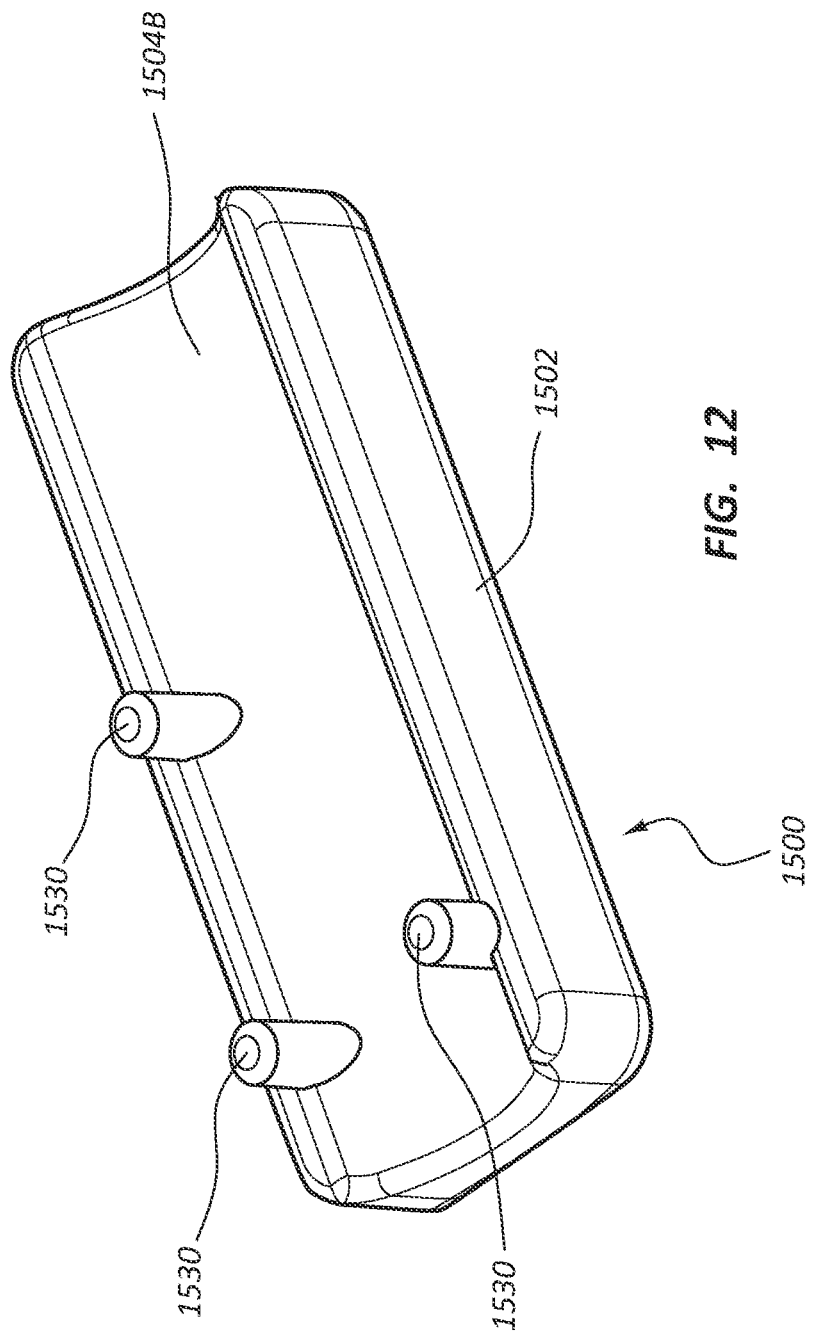
FIG. 12 is a perspective view of a portion of a magnetizer according to one embodiment.

Note that the two holes/two post embodiment of FIGS. 9A-11C is but one example of an orientation key system. It is appreciated that the size, number, shape, position, and other configuration of the posts and holes can vary from what is described herein. Indeed, more than two posts can be employed, as is seen in the embodiment of the magnetizer body 1502 of FIG. 12, wherein three posts 1530 are included. In other embodiments, differently shaped features other than posts can be disposed on magnetizer body and/or tray to operate as key features. In one embodiment, the posts can be included on the tray while corresponding holes are included on the magnetizer body. In another embodiment, a mixed combination of posts and holes are included on both the magnetizer and the tray. In yet another embodiment, a component other than a tray can be used to hold the insertion tool/needle and mate with the magnetizer. In light of the above discussion, it is appreciated that the orientation key system further serves as a visual cue for enabling the clinician to understand the proper mode for placing the tray (or medical device) on the magnetizer.

In the present embodiment, an RFID tag 1550, or other mode of identification, can be attached to the tray 1510, such as is seen in FIGS. 9A-9C and 11A-11C. A corresponding RFID reader 1560 can be positioned under the first portion 1504A of the magnetizer body receptacle 1504 (FIG. 9C) to read the RFID tag 1550 of the tray 1510 when it is positioned on the magnetizer body 1502. The RFID reader 1560 includes an interface, such as a USB interface 1564 to enable it to be powered by and operably connect with the system 1110 (see also FIG. 16). In this way, the guidance system 1110 (FIGS. 15, 16)—of which the magnetizer 1500 is a part in the present embodiment—can read the information encoded on the tray RFID tag 1550 to identify the insertion tool 10 and determine such characteristics as the size, length, type, material, etc. of the insertion tool or its needle 16 (including needle length, gauge, etc.) (or other medical device) disposed therein. This in turn enables the guidance system 1110 to configure itself for specific use with the insertion tool 10 and needle 16 corresponding to the information included on the RFID tag 1550.

Such an RFID system can also prevent unauthorized components from being usable with the guidance system 1110 by locking out operation of the needle tracking system when no RFID tag is detected upon tray mating with the magnetizer body, for instance, or when the tag has previously been read by the RFID reader 1560 a predetermined number of times.

Figure 13:
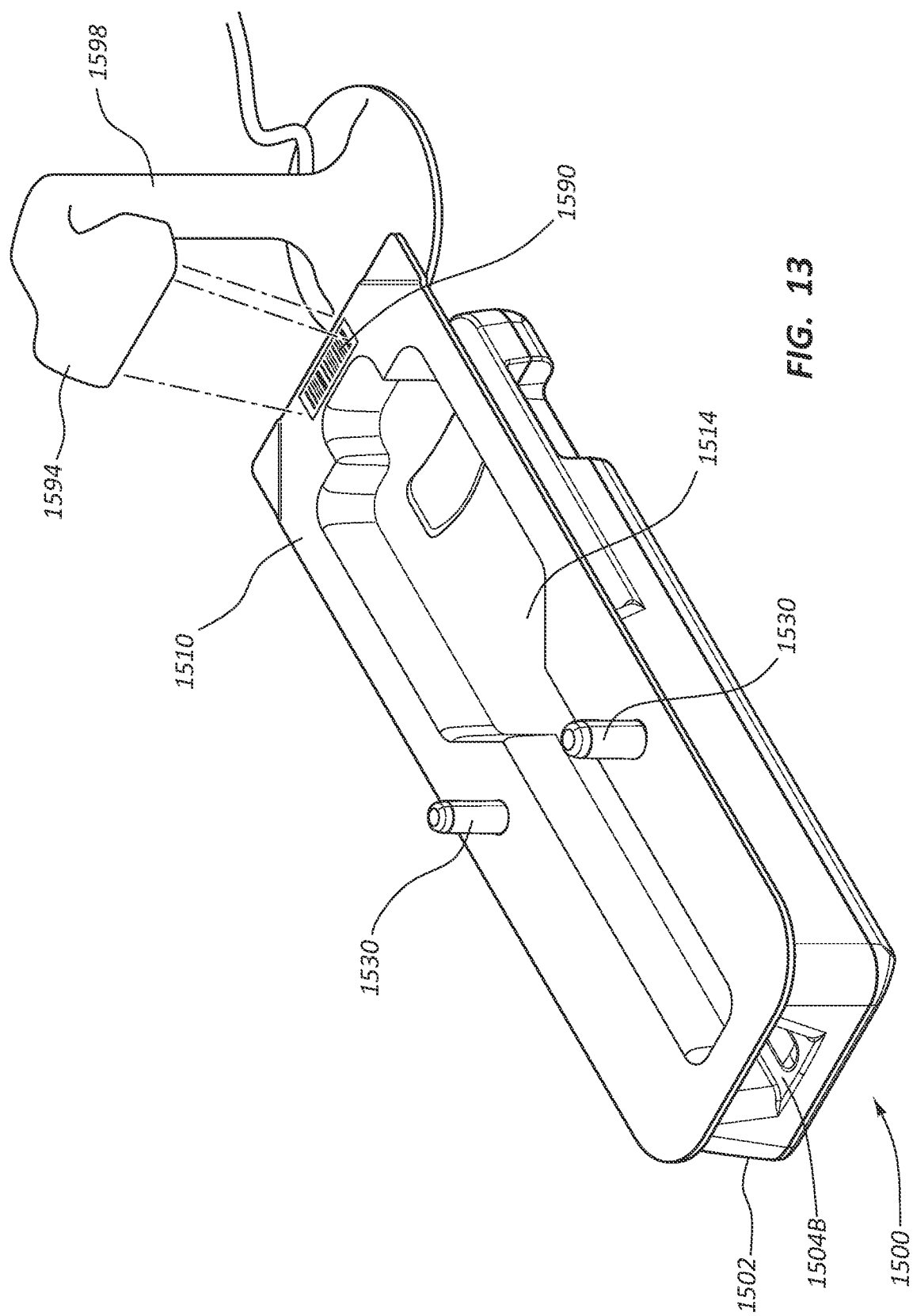
FIG. 13 is a perspective view of a magnetizer according to one embodiment.
Figure 14:
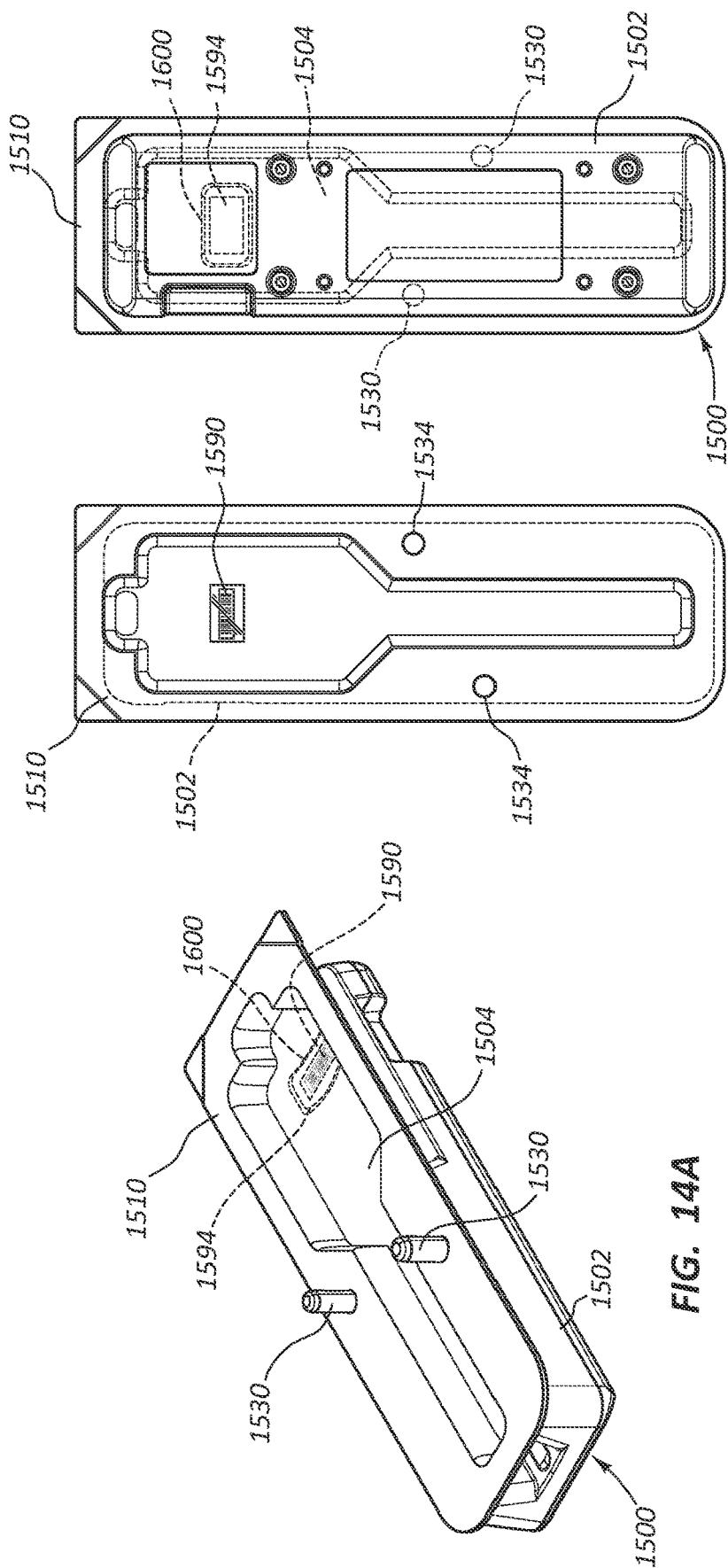
FIGS. 14A-14C depict various views of a magnetizer and tray assembly according to one embodiment.

FIG. 13 depicts another system for identifying the insertion tool 10/medical device, including a barcode 1590 disposed on the tray 1510 and a barcode scanner 1594 positioned on a support arm 1598 to read the barcode when the tray is placed on the magnetizer 1500. FIGS. 14A-14C depict another variation, wherein a window 1600 is included in the magnetizer body receptacle 1504. The barcode scanner 1594 is disposed below the window 1600. A bottom surface of the tray 1510 includes the barcode 1590 thereon. The barcode 1590 is positioned such that it aligns with the window 1600 when the tray is received into the magnetizer body receptacle 1504, thus allowing the barcode scanner 1594 to read the barcode and identify the insertion tool/medical device disposed in the tray. It is appreciated that various other barcode configurations can be included with the magnetizer, as well as other identification schemes.

Note that, though permanent magnets are depicted and discussed herein, other magnetic components can be employed in other embodiments, including an electromagnet, etc. Also note that further details regarding the sensor array and the guidance system employed to detect the magnetic field of the magnetized needle/medical device can be found in the following U.S. patents and patent application publications: 2014/0257080; 2014/0257104; 9,155,517; 9,257,220; 9,459,087; and 9,597,008, each of which is incorporated by reference in its entirety into this application.

Embodiments of the invention may be embodied in other specific forms without departing from the spirit of the present disclosure. The described embodiments are to be considered in all respects only as illustrative, not restrictive. The scope of the embodiments is, therefore, indicated by the appended claims rather than by the foregoing description. All changes that come within the meaning and range of equivalency of the claims are to be embraced within their scope.

What is claimed is:

1. A magnetizing system comprising a magnetizer configured to magnetize a needle associated with a medical device, and a tray configured to removably join with the magnetizer, the magnetizer comprising:
    a body;
    a magnetic component included with the body; and
    an orientation key system including a first key feature included with the body of the magnetizer, the first key feature configured to cooperatively and removably mate with a second key feature included with the tray so as to position the needle of the medical device in a desired orientation with respect to the magnetic component.

2. The system according to claim 1, wherein the magnetizer further includes an RFID reader configured to read an RFID tag included with the medical device.

3. The system according to claim 1, wherein the magnetic component includes a plurality of permanent magnets positioned in a multipole arrangement.

4. The system according to claim 1, wherein the needle is included in an insertion tool configured to assist in inserting a catheter into the body of a patient.

5. The system according to claim 4, wherein the insertion tool is disposed in the tray that is removably positionable on the magnetizer.

6. The system according to claim 1, wherein the first key feature includes a cavity defined in the body of the magnetizer, and wherein the second key feature includes a protrusion defined on the tray.

7. The system according to claim 1, wherein the first key feature includes first and second posts on the body of the magnetizer, and wherein the second key feature includes first and second holes defined in the tray.

8. The system according to claim 7, wherein the first and second posts are positioned in an offset configuration on the body of the magnetizer, and wherein the first and second holes in the tray are offset so as to respectively receive the first and second posts.

9. The system according to claim 1, wherein the orientation key system is configured to inhibit placement of the tray on the magnetizer in an erroneous orientation.

10. The system according to claim 7, wherein the first post defines a diameter that is different from a diameter defined by the second post, and wherein the first hole is sized to receive the first post and the second hole is sized to receive the second post.

11. The system according to claim 1, further comprising a RFID tag included with the tray.

* * * * *